United States Patent
Leevy et al.

(10) Patent No.: US 8,041,409 B2
(45) Date of Patent: *Oct. 18, 2011

(54) METHOD AND APPARATUS FOR MULTI-MODAL IMAGING

(75) Inventors: Warren M. Leevy, Granger, IN (US); Gilbert Feke, Durham, CT (US); Douglas L. Vizard, Durham, CT (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/460,010

(22) Filed: Jul. 10, 2009

(65) Prior Publication Data
US 2009/0324048 A1    Dec. 31, 2009

Related U.S. Application Data

(63) Continuation-in-part of application No. 11/221,530, filed on Sep. 8, 2005, now Pat. No. 7,734,325, and a continuation-in-part of application No. 12/354,830, filed on Jan. 16, 2009.

(60) Provisional application No. 61/079,847, filed on Jul. 11, 2008.

(51) Int. Cl.
*A61B 6/00* (2006.01)
(52) U.S. Cl. .......... 600/407; 600/425; 600/476; 378/44; 378/51; 250/339.06; 250/336.1
(58) Field of Classification Search ................... 250/367; 378/62; 382/132, 264; 600/407
See application file for complete search history.

(56) References Cited

U.S. PATENT DOCUMENTS

| | | |
|---|---|---|
| 1,609,703 A | 12/1926 | Eggert et al. |
| 3,717,764 A | 2/1973 | Fujimura et al. |
| 3,936,644 A | 2/1976 | Rabatin |
| 4,028,550 A | 6/1977 | Weiss et al. |
| 4,088,894 A | 5/1978 | Rabatin |
| 4,107,070 A | 8/1978 | Everts et al. |
| 4,208,470 A | 6/1980 | Rabatin |
| 4,232,227 A | 11/1980 | Finkenzeller et al. |
| 4,394,737 A | 7/1983 | Komaki et al. |
| 4,446,365 A | 5/1984 | Ong et al. |
| 4,675,529 A | 6/1987 | Kushida |
| 4,710,637 A | 12/1987 | Luckey et al. |
| 4,829,188 A | 5/1989 | Shinomiya et al. |

(Continued)

FOREIGN PATENT DOCUMENTS
EP      1 111 625 A2    6/2001
(Continued)

OTHER PUBLICATIONS

Commonly assigned, U.S. Appl. No. 12/381,599, filed Mar. 13, 2009, by: Gilbert Feke et al.

(Continued)

*Primary Examiner* — Tse Chen
*Assistant Examiner* — Vani Gupta

(57) ABSTRACT

A method and apparatus for imaging a subject animal. The method comprises the steps of treating the animal with an x-ray contrast agent and an imaging agent; supporting the animal in an immobilized state on a support member; acquiring an x-ray anatomical image of the animal; acquiring an optical, dark-field image of the animal; and registering the x-ray anatomical image and the optical image, whereby features of the optical image can be observed in relation to features of the anatomical image.

16 Claims, 17 Drawing Sheets

U.S. PATENT DOCUMENTS

| | | | |
|---|---|---|---|
| 4,870,279 A | 9/1989 | Cueman et al. | |
| 4,891,527 A | 1/1990 | Rabatin | |
| 4,898,175 A | 2/1990 | Noguchi | |
| 5,069,982 A | 12/1991 | Zegarski | |
| 5,501,225 A | 3/1996 | Wilson | |
| 5,663,005 A | 9/1997 | Dooms et al. | |
| 5,717,791 A | 2/1998 | Labaere et al. | |
| 5,748,768 A | 5/1998 | Sivers et al. | |
| 5,830,629 A | 11/1998 | Vizard et al. | |
| 6,227,704 B1 | 5/2001 | Bani-Hashemi et al. | |
| 6,229,873 B1 | 5/2001 | Bani-Hashemi et al. | |
| 6,269,177 B1 | 7/2001 | Dewaele et al. | |
| 6,278,765 B1 | 8/2001 | Berliner | |
| 6,346,707 B1 | 2/2002 | Vizard et al. | |
| 6,379,044 B1 | 4/2002 | Vastenaeken et al. | |
| 6,416,800 B1 | 7/2002 | Weber et al. | |
| 6,424,750 B1 | 7/2002 | Colbeth et al. | |
| 6,444,988 B1 | 9/2002 | Vizard | |
| 6,447,163 B1 | 9/2002 | Bani-Hashemi et al. | |
| 6,459,094 B1 | 10/2002 | Wang et al. | |
| 6,473,489 B2 | 10/2002 | Bani-Hashemi et al. | |
| 6,495,812 B1 | 12/2002 | Wurm et al. | |
| 6,615,063 B1 | 9/2003 | Ntziachristos et al. | |
| 7,113,217 B2 | 9/2006 | Nilson et al. | |
| 7,190,991 B2 | 3/2007 | Cable et al. | |
| 7,198,404 B2* | 4/2007 | Navab et al. | 378/206 |
| 7,338,651 B2* | 3/2008 | Bornhop et al. | 424/9.3 |
| 7,394,053 B2 | 7/2008 | Frangioni et al. | |
| 7,734,325 B2* | 6/2010 | Vizard et al. | 600/407 |
| 2001/0012386 A1 | 8/2001 | Struye et al. | |
| 2003/0082104 A1 | 5/2003 | Mertelmeier | |
| 2003/0211158 A1 | 11/2003 | Frechet et al. | |
| 2004/0004193 A1 | 1/2004 | Nilson et al. | |
| 2004/0089817 A1 | 5/2004 | Long et al. | |
| 2004/0202360 A1 | 10/2004 | Besson | |
| 2004/0249260 A1 | 12/2004 | Wang et al. | |
| 2005/0148846 A1 | 7/2005 | Cable et al. | |
| 2005/0175538 A1 | 8/2005 | Coquoz et al. | |
| 2005/0237423 A1 | 10/2005 | Nilson et al. | |
| 2006/0064000 A1 | 3/2006 | Vizard et al. | |
| 2006/0111613 A1 | 5/2006 | Boutillette et al. | |
| 2006/0118742 A1 | 6/2006 | Levenson et al. | |
| 2006/0173354 A1 | 8/2006 | Ntziachristos et al. | |
| 2006/0210135 A1 | 9/2006 | Kanegae | |
| 2007/0016077 A1 | 1/2007 | Nakaoka et al. | |
| 2007/0063154 A1 | 3/2007 | Chen et al. | |
| 2007/0087445 A1 | 4/2007 | Tearney et al. | |
| 2007/0217713 A1 | 9/2007 | Milanfar et al. | |
| 2007/0238957 A1 | 10/2007 | Yared | |
| 2007/0281322 A1 | 12/2007 | Jaffe et al. | |
| 2008/0049893 A1 | 2/2008 | Bartzke et al. | |
| 2008/0281322 A1 | 11/2008 | Sherman et al. | |
| 2009/0086908 A1 | 4/2009 | Harder et al. | |
| 2009/0159805 A1 | 6/2009 | Feke et al. | |

FOREIGN PATENT DOCUMENTS

| | | |
|---|---|---|
| EP | 1 304 070 A2 | 4/2003 |
| EP | 1 619 548 A2 | 1/2006 |
| JP | 58-17544 U | 7/1981 |
| JP | 02-031144 | 2/1990 |
| JP | 02-052246 | 2/1990 |
| JP | 09-309845 | 12/1997 |
| JP | 11-244220 | 9/1999 |
| JP | 2001-255607 | 9/2001 |
| JP | 2001-299786 | 10/2001 |
| JP | 2003-028995 | 1/2003 |
| JP | 2004-121289 | 4/2004 |
| JP | 2005-049341 | 2/2005 |
| JP | 2005-164577 | 6/2005 |
| WO | 2004/018185 A2 | 9/2004 |
| WO | 2004/081865 A2 | 9/2004 |
| WO | 2004/089204 A1 | 10/2004 |
| WO | 2004/108902 A2 | 12/2004 |
| WO | 2005/027730 A2 | 3/2005 |
| WO | 2007/032940 A2 | 3/2007 |

OTHER PUBLICATIONS

Commonly assigned, U.S. Appl. No. 12/475,623, filed Jun. 1, 2009, by Gilbert Feke et al.

Nature Methods, "Harnessing multimodality to enhance quantification and reproducibility of in vivo molecular imaging data", by Gilbert D. Feke et al., Nov. 2008.

Biochem Biophys Res Commun, Inspiration for Life Science, "Anti Human Galectin 3 Polyelonal Antibody", by W. Zhu, 280:11831188, 2001.

IEEE Transactions on Nuclear Science, "Iodine 125 Imaging in Mice Using NaI(TI)/Flat Panel PMT Integral Assembly", by M.N. Cinti et al., vol. 54, No. 3, Jun. 2007, pp. 461-468.

Mat. Res. Soc. Symp. Proc., "Optimising of the Physico-Chemical Properties of a Novel Barium Sulphate Preparation for the X-Ray Examination of the Intestine", by Barbara Laermann et al., vol. 550, 1999 Materials Research Society, pp. 59-64.

Am. Assoc. Phys. Med., "MicroCT scanner performance and considerations for vascular specimen imaging", by Michael Marxen et al., Med. Phys. 31 (2), Feb. 2004.

Rat Atlas Project, Internet Study: Hubei Bioinformatics and Molecular Imaging Key Laboratory, The Key Laboratory of Biomedical Photonics of Ministry of Education, College of Life Science and Technology, Huazhong University of Science and Technology, http://202.114.29.53/vch/mice/index.aspx.

The Scientist: "The Bare Bones of Animal Imaging", by Linda Sage, vol. 19, Issue 4, pp. 36, Feb. 28, 2005, XP-002357416.

Cosmo Bio News, Kodak Image Station 2000MM, Cosmo Bio News No. 43, pp. 18, Mar. 2004 (Foreign with English translation) XP-002357415—advertisement.

Kodak Image Station 2000MM Multi-Modal Imager, Kodak Scientific Imaging Systems-advertisment.

User's Manual "Kodak Image Station 2000MM", IB2110305, Nov. 2003.

User's Manual, "Kodak Image Station 2000R", Aug. 2002.

"Monomolecular Multimodal Fluorescence-Radiosotope Imaging Agents", Bioconjugate Chemistry, 16(5), pp. 1232-1239, 2005.

Proceedings of the American Thoracic Society, "Micro-Computed Tomography of the Lungs and Pulmonary-Vascular System", by Erik L. Ritman, 2 pp. 477-480 2005.

The Journal of Nuclear Medicine, "Significance of Incidental $^{18}$F-FDG Accumulations in the Gastrointestical Tract in PET/CT: Correlation with Endoscopic and Histopathologic Results", by Ehab M. Kamel et al., vol. 45, No. 11, pp. 1804-1810, 2004.

"Research Takes Many Directions," The Scientist, vol. 303, No. 5657, single page Kodak ad, Jan. 23, 2004.

Zhang et al., "Monomolecular Multimodal Fluorescence-Radioisotope Imaging Agents," Bioconjugate Chemistry, 16(5), pp. 1232-1239, 2005.

Corresponding WO = PCT/us2005/032504, International Preliminary Report on Patentability, dated Mar. 27, 2007, 8 pages.

International Search Report, International Application No. PCT/US2005/032504, dated Dec. 23, 2005.

International Search Report, International Application No. PCT/US2008/010304, dated Dec. 8, 2008.

International Search Report, International Application No. PCT/US2009/000457, dated Aug. 21, 2009.

Kodak Image Station 2000MM Multimodal Imaging System, Internet web address: http://www.kodak.com/US/en/health/scientific/products/imgstation2000MM/index.shtml-Sep. 16, 2004. (1 page).

Hussain et al., Enhanced Oral Uptake of Tomato Lectin-Conjugated Nanoparticles in the Rat, Pharmaceutical Research, vol. 14, No. 5, 1997, pp. 613-618.

V.P. Torchilin, Polymer-coated long-circulating microparticulate pharmaceuticals, J. Microencapsulation, 1998, vol. 15, No. 1, pp. 1-19.

Alyautdin et al., Delivery of Loperamide Across the Blood-Brain Barrier with Polysorbate 80-Coated Polybutylcyanoacrylate Nanoparticles, Pharmaceutical Research, vol. 14, No. 3, 1997, pp. 325-328.

Y. Kwon et al., Enhanced antigen presentation and immunostimulation of dendritic cells using acid-degradable cationic nanoparticles, Journal of Controlled Release 105, 2005, pp. 199-212.

Harlow et al., Antibodies—A Laboratory Manual, Chapter 5-Immunizations, 1988, pp. 91-113.

Winter et al., Man-made antibodies, Nature—vol. 349, Jan. 24, 1991, pp. 293-299.

Köhler et al., Derivation of specific antibody-producing tissue culture and tumor lines by cell fusion, Medical Research Council Laboratory of Molecular Biology, Cambridge, Eur. J. Immunol., 1976, vol. 6, pp. 511-519.

LoBuglio et al., Mouse/human chimeric conoclonal antibody in man: Kinetics and immune response, Proc. Natl. Acad. Sci., vol. 86, Jun. 1989 Immunology, pp. 4220-4224.

De Verdiè, et al., Reversion of multidrug resistence with polyalkycyanoacrylate nanoparticles: towards a mechanism of action, BJC British Journal of Cancer, 1997, vol. 76 (2), pp. 198-205.

Sharma et al., Novel Taxol® Formulation: Polyvinylpyrrolidone Nanoparticle-Encapsulated Taxol® for Drug Delivery in Cancer Therapy, Oncology Research, vol. 8, Nos. 7/8, pp. 281-286, 1986.

Zobel et al., Cationic Polyhexylcyanoacrylate Nanoparticles as Carriers for Antisense Oligonucleotides, Antisense & Nucleic Acid Drug Development, vol. 7, 1997, pp. 483-493.

Burke et al., Acid-Base Equilibria of Weak Polyelectrolytes in Multilayer Thin Films, Langmuir, 2003, vol. 19, No. 8, pp. 3297-3303.

Hrkach et al., Nanotechnology for biomaterials engineering; structural characterization of amphiphilic polymeric nanoparticles by $^1$H NMR spectroscopy, Biomaterials, vol. 18, No. 1, 1997, pp. 27-30.

G. Volkheimer, Übersicht, Persorption von Mikropartikeln, Pathologies, 1993, vol. 14, pp. 247-252.

Moghimi et al., Nanomedicine: current status and future prospects, The FASEB Journal, vol. 19, Mar. 2005, pp. 311-330.

Soukchareun et al., Preparation and Characterization of Antisense Oligonucleotide—Peptide Hybrids Containing Viral Fusion Peptides, Bioconjugate Chem, 1995, vol. 6, pp. 43-53.

G. Kwon et al., Block copolymer micelles as long-circulating drug vehicles, Advanced Drug Delivery Reviews, vol. 16, 1995, pp. 295-309.

Labhasetwar et al., Nanoparticle drug delivery system for restenosis, Advanced Drug Delivery Reviews, vol. 24, 1997, pp. 63-85.

Co-pending U.S. Appl. No. 11/400,935, filed Apr. 10, 2006, Publication No. 2000/0238656, Harder et al., Functionalized Poly(Ethylene Glycol).

Co-pending U.S. Appl. No. 11/165,849, filed Jun. 24, 2006, Publication No. 2006/0293396, Bringley et al., Nanoparticle Based Substrate for Image Contrast Agent Fabrication.

Yamashita et al., Mist particle diameters are related to the toxicity of waterproofing sprays: Comparison between toxic and non-toxic products, vol. 39, 71-74.

Cleare et al., "An Experimental Study of the Mottle Produced by X-Ray Intensifying Screens," The Am. J. of Roent. and Rad. Physics, vol. 88, No. 1, pp. 168-174, Jul. 1962.

P. Mitchell, "Picture Perfect: Imaging Gives Biomarkers New Look", *Pharma DD*, vol. 1, No. 3, pp. 1-5 (2006).

Virostko et al., Molecular Imaging, vol. 3, No. 4, Oct. 2004, pp. 333-342, Factors Influencing Quantification of In Vivo Bioluminescence Imaging: Application to Assessment of Pancreatic Islet Transplants.

Da Silva et al., ScienceDirect, Nuclear Instruments and Methods in Physics Research, Design of a small animal multimodality tomographer for X-ray and optical coupling: Theory and experiments, 2007, pp. 118-121.

Kruger et al., HYPR-spectral photoacoustic CT for preclinical imaging, Photons Plus Ultrasound Imaging and Sensing 2009, Proc. of SPIE, vol. 7177, 10 pages.

Corresponding CN = CN 200580031808.5—SIPO First Office Action dated Dec. 4, 2009. 14 pages.

\* cited by examiner

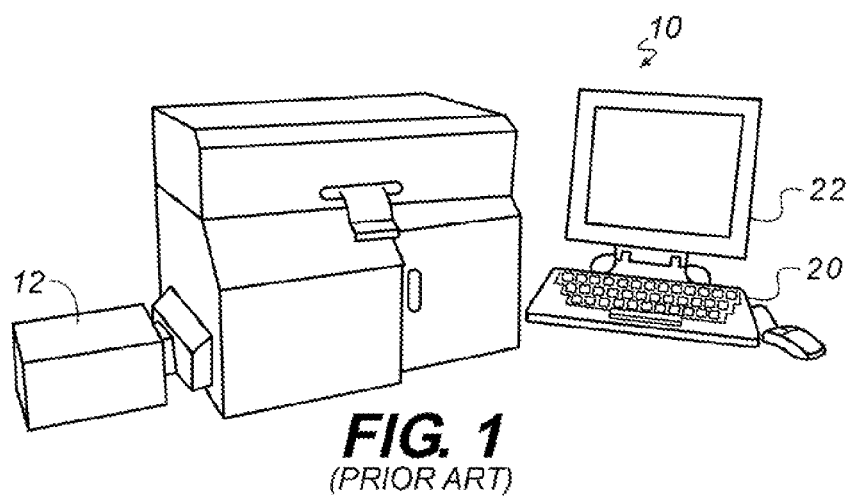
FIG. 1
(PRIOR ART)
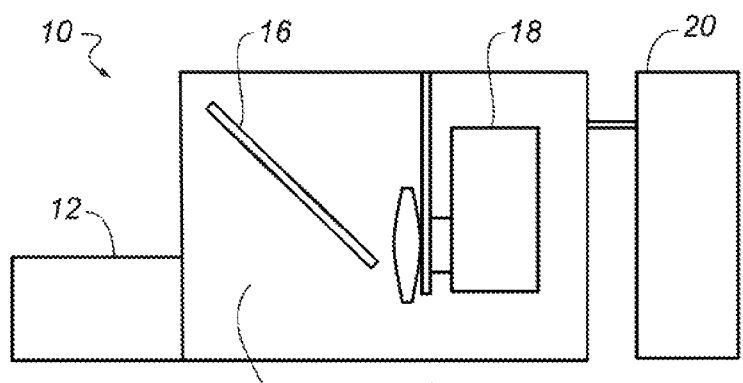
FIG. 2
(PRIOR ART)
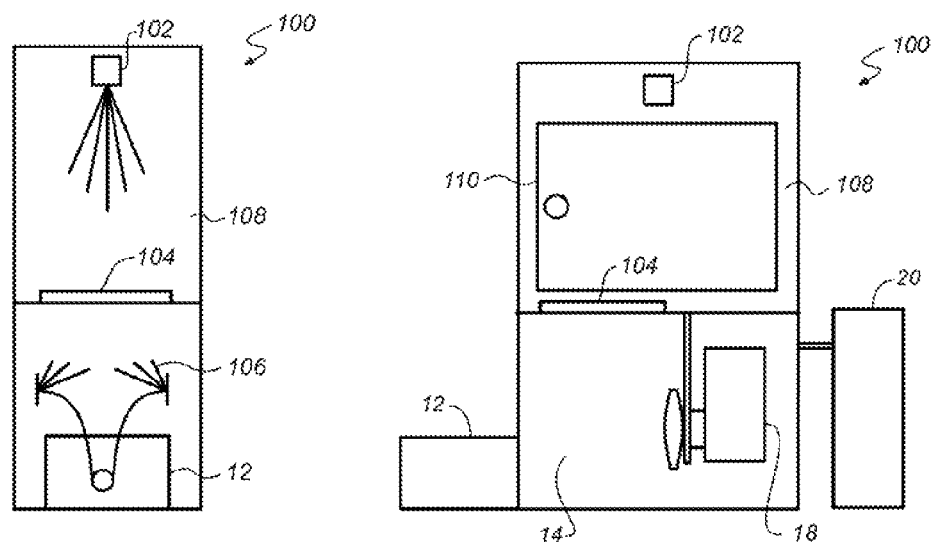
FIG. 3A    FIG. 3B

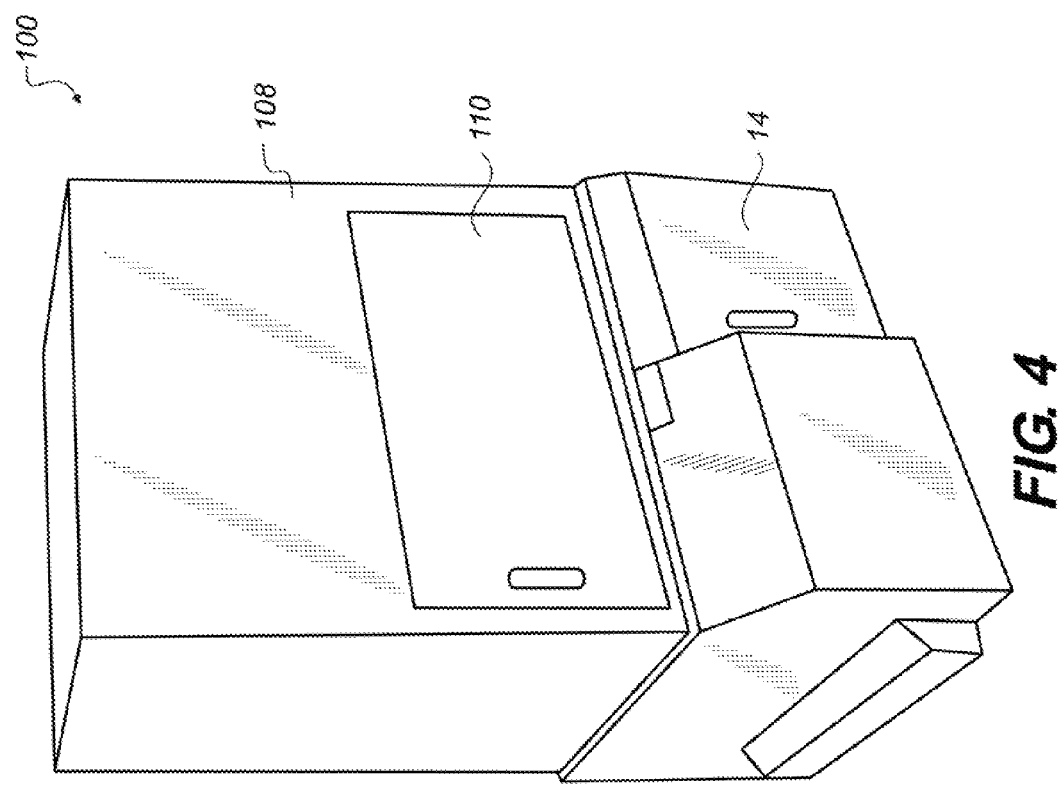

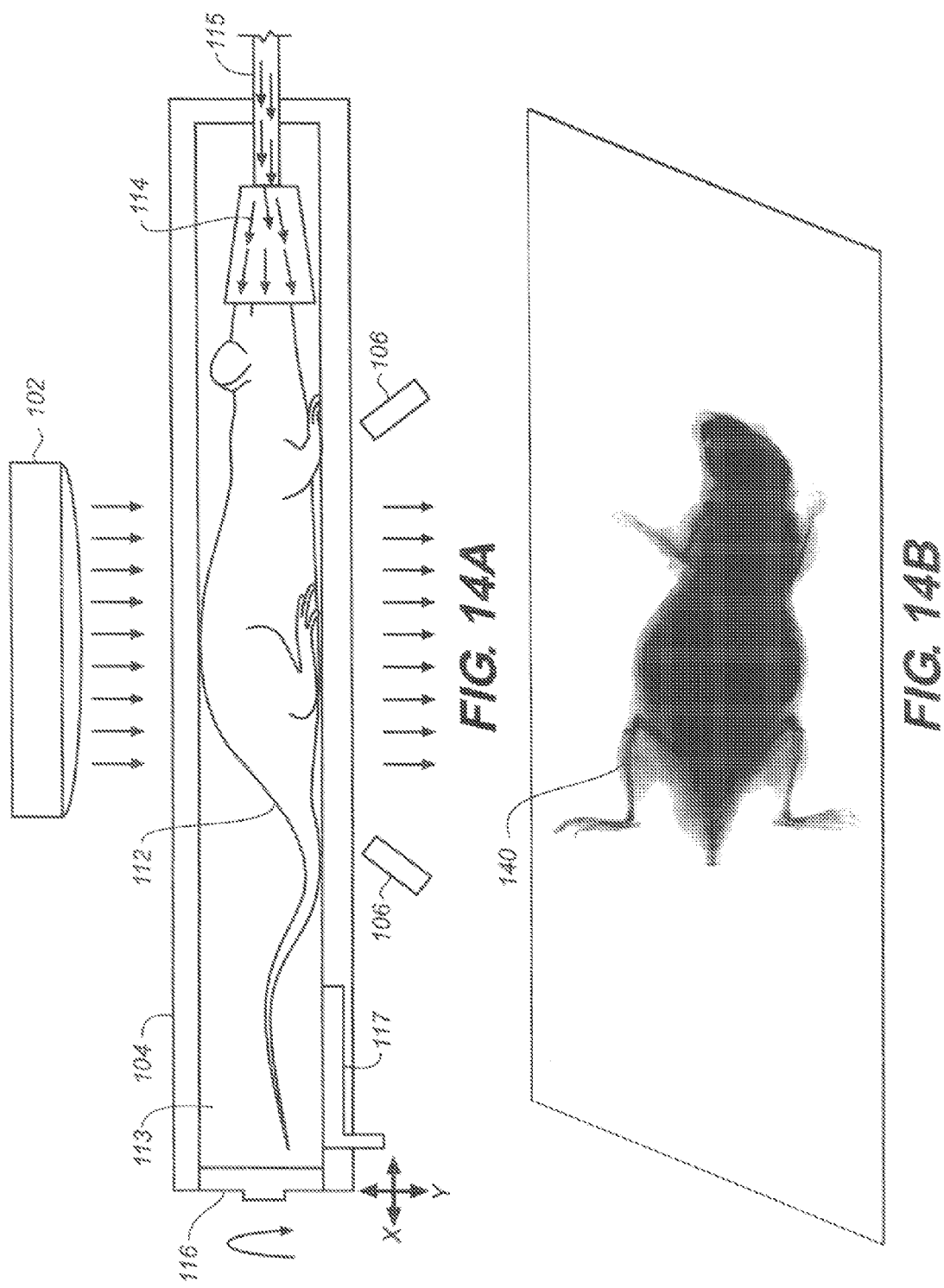

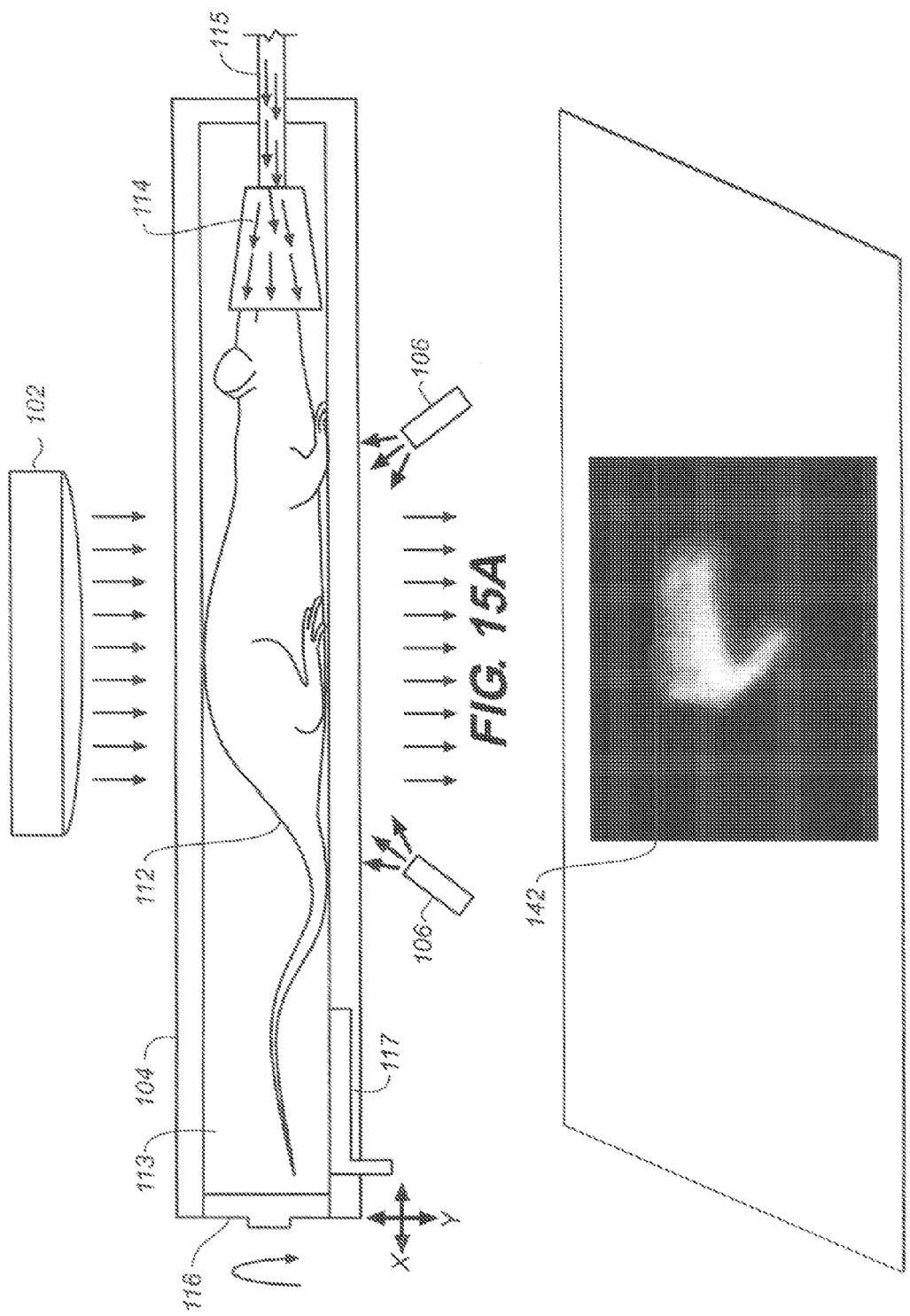

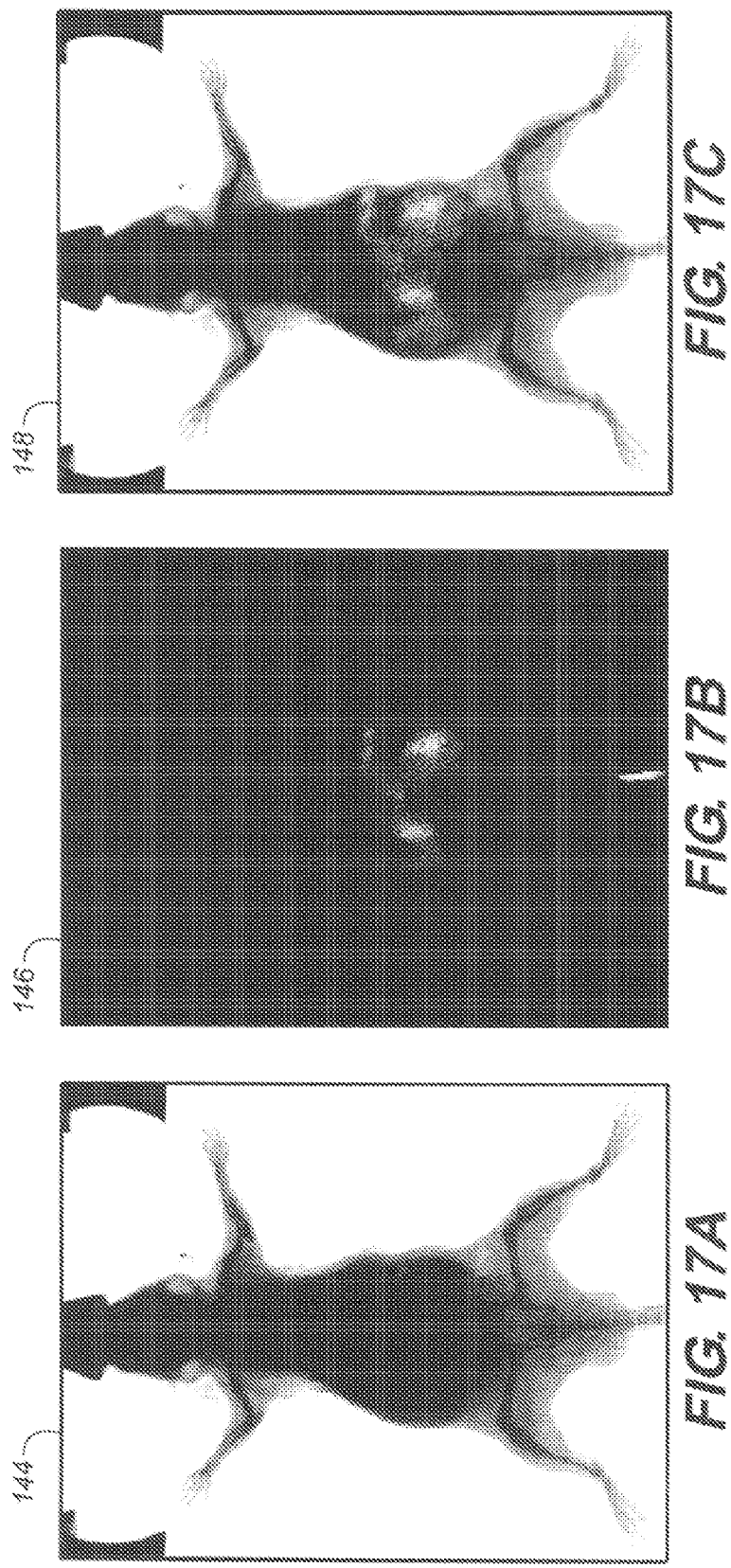

METHOD AND APPARATUS FOR MULTI-MODAL IMAGING

CROSS REFERENCE TO RELATED APPLICATIONS

Priority is claimed from copending, commonly assigned U.S. Provisional Patent Application Ser. No. 61/079,847 filed Jul. 11, 2008 by Leevy et al and entitled APPARATUS AND METHOD FOR MULTI-MODAL IMAGING, the contents of which are incorporated by reference into this specification.

This application is a continuation-in-part of the following commonly assigned, copending U.S. patent applications, the contents of each of which also are incorporated by reference into this specification:

U.S. Ser. No. 11/221,530, filed Sep. 8, 2005 by Vizard et al, entitled APPARATUS AND METHOD FOR MULTI-MODAL IMAGING, which issued on Jun. 8, 2010 as U.S. Pat. No. 7,734,325; and U.S. Ser. No. 12/354,830 filed Jan. 16, 2009 by Feke et al, entitled APPARATUS AND METHOD FOR MULTI-MODAL IMAGING.

FIELD OF THE INVENTION

The invention relates generally to the field of imaging systems, and more particularly to the imaging of objects. More specifically, the invention relates to an improved apparatus and method that enable analytical imaging of objects (for example, small animals and tissue) in differing modes, including bright-field, dark-field (e.g., luminescence and fluorescence), and x-ray and radioactive isotopes.

BACKGROUND OF THE INVENTION

Electronic imaging systems are well known for enabling molecular imaging. An exemplary electronic imaging system 10 (shown in FIG. 1 and diagrammatically illustrated in FIG. 2) is the Image Station 2000 MM Multimodal Imaging System formerly available from the Eastman Kodak Company. System 10 includes a light source 12, an optical compartment 14 which can include a mirror 16, a lens and camera system 18, and a communication and computer control system 20 which can include a display device, for example, a computer monitor 22. Camera and lens system 18 can include an emission filter wheel for fluorescent imaging. Light source 12 can include an excitation filter selector for fluorescent excitation or bright field color imaging. In operation, an image of an object is captured using lens and camera system 18. System 18 converts the light image into an electronic image, which can be digitized. The digitized image can be displayed on display device 22, stored in memory, transmitted to a remote location, processed to enhance the image, used to print a permanent copy of the image, or all of these.

SUMMARY OF THE INVENTION

An object of the present invention is to provide an improved method and apparatus for enabling analytical imaging of an object. Another object of the present invention is to provide such a method and apparatus that use differing imaging modes.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention, there is provided an improved method for using an imaging system for imaging an object. An example of such an imaging system useful in the inventive method includes a support member adapted to receive the object in an immobilized state. The system also includes first means for imaging the immobilized object in a first imaging mode to capture a first image, and second means for imaging the immobilized object in a second imaging mode, different from the first imaging mode, to capture a second image. The first imaging mode is selected from the group: x-ray mode and radio isotopic mode. The second imaging mode is selected from the group: bright-field mode and dark-field mode. A removable phosphor screen may be employed when the first image is captured, but not employed when the second image is captured. The phosphor screen is adapted to transduce ionizing radiation to visible light. The phosphor screen is adapted to be removable without moving the immobilized object. The system can further include means for generating a third image comprised of the first and second image.

A first embodiment of the inventive method is useful for imaging a subject animal. The method includes a step of treating the animal with both an x-ray contrast agent and an optical imaging agent, which may be targeted or non-targeted agents, or both. As used in this specification and as understood by those skilled in the art, the terms "targeted agent" refer in general to agents that accumulate in specific tissues or organs of the animal's body by molecular targeting, such as antibodies, peptides and the like attached to the agents. Similarly, the terms "non-targeted agents" refer in general to agents that accumulate in specific tissues or organs by physiological processes, such as the gastrointestinal process or the renal process. The method of the invention further may include steps of supporting the animal in an immobilized state; acquiring an x-ray anatomical image of the immobilized animal; acquiring an optical dark-field image, such as a fluorescence image or a luminescence image, of the immobilized animal; and registering the x-ray anatomical image and the optical dark-field image, whereby features of the optical image can be observed in relation to features of the anatomical image. The x-ray contrast agent and optical imaging agent may be administered simultaneously or sequentially to the animal. In accordance with the invention, the x-ray contrast agent may be targeted while the optical imaging agent is non-targeted; or the x-ray contrast agent may be non-targeted while the optical imaging agent is targeted; or both agents may be targeted; or both agents may be non-targeted. The x-ray image and the optical image may be acquired using a common, shared focal plane.

A second embodiment of the inventive method may include steps of treating the animal with an x-ray contrast agent and an optical imaging agent, as in the first embodiment; supporting the animal in an immobilized state on a support member; providing a phosphor plate adapted to be disposed proximate the support member when capturing a first image; with the phosphor plate disposed proximate the support member, imaging the immobilized animal in a first imaging mode to capture the first image, the first imaging mode being an x-ray mode; removing the phosphor plate from proximate the support member, after capturing the first image and without moving the immobilized animal and the support member; and with the phosphor plate removed from proximate the support member, imaging the immobilized animal in a second imaging mode to capture a second image, the second imaging mode being a dark-field mode. The method may include a further step of generating a third image by merging the first and second images, whereby features of the second image can be observed in relation to features of the first image. Again, the x-ray contrast agent and optical imaging agent may be administered simultaneously or sequentially to the animal. Also, the x-ray contrast agent may be targeted while the imaging agent is untargeted; or the x-ray contrast agent may be non-targeted while the imaging agent is targeted; or both agents may be targeted; or both agents may be untargeted. The x-ray image and the optical image may be acquired using a common, shared focal plane.

A third embodiment of the inventive method may include steps of treating the animal with an x-ray contrast agent and an optical imaging agent as in the first and second embodiments; supporting the animal in an immobilized state on a support member; providing a phosphor plate movable relative to the support member, without disturbing the immobilized animal and the support member, between a first position wherein the phosphor plate is in optical registration with the support member and a second position wherein the phosphor plate is not in optical registration with the support member; capturing an x-ray image of the immobilized animal when the phosphor plate in disposed in the first position; and capturing a dark-field image of the immobilized animal when the phosphor plate in disposed in the second position. The method may include further steps of generating a third image by merging the first and second images, whereby features of the second image can be observed in relation to features of the first image; and displaying, transmitting, processing, or printing, the third image. As in the first two embodiments, the x-ray contrast agent and optical imaging agent may be administered simultaneously or sequentially to the animal. Also, the x-ray contrast agent may be targeted while the imaging agent is untargeted; or the x-ray contrast agent may be non-targeted while the imaging agent is targeted; or both agents may be targeted; or both agents may be untargeted. The x-ray image and the optical image may be acquired using a common, shared focal plane.

A fourth embodiment of the invention concerns an apparatus for imaging a subject animal. This apparatus may include first imaging means for imaging such an animal in a first imaging mode to capture a first image, the first imaging mode being selected from the group: x-ray mode and radio isotope mode; second imaging means for imaging such an animal in a second imaging mode that uses light from the immobilized animal to capture a second image, the second imaging mode being selected from the group: bright-field imaging mode and dark-field imaging mode; and a support stage, fixedly mounted in the apparatus, for receiving such an animal in an immobilized state such that the animal is immobilized in the apparatus during imaging by the first and second imaging means without movement of the animal from the support stage or movement of the support stage between capture of the first and second images.

The fourth embodiment also may include movable phosphor plate to transduce ionizing radiation from the first imaging means to visible light, the phosphor plate being mounted to be moved, without moving the immobilized animal and support stage, between a first position proximate the support stage during capture of the first image and a second position not proximate the support stage during capture of the second image.

A fifth embodiment of the invention concerns a method for imaging a subject animal. This method may include steps of providing a fixed support stage; receiving the animal on the support stage in an immobilized state; imaging the immobilized animal on the support stage in a first imaging mode to capture a first image, the first imaging mode being selected from the group: x-ray mode and radio isotope mode; and without moving the animal or the support stage, imaging the animal on the support stage in a second imaging mode that uses light from the immobilized animal to capture a second image, the second imaging mode being selected from the group: bright-field imaging mode and dark-field imaging mode.

This fifth embodiment also may include steps of providing a movable phosphor plate to transduce ionizing radiation from the first imaging means to visible light; and moving the phosphor plate, without moving the immobilized animal and support stage, between a first position proximate the support stage during capture of the first image and a second position not proximate the support stage during capture of the second image. This method further may include steps of treating the animal with an x-ray contrast agent and an optical imaging agent; and registering the first image with the second image, whereby features of the second image may be observed in relation to features of the first image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1 shows a perspective view of an exemplary prior art electronic imaging system, of a type useful in accordance with the method of the present invention.

FIG. 2 shows a diagrammatic view of the system of FIG. 1.

FIG. 3A shows a diagrammatic side view of the imaging system of FIGS. 1 and 2.

FIG. 3B shows a diagrammatic front view of the imaging system of FIG. 3A.

FIG. 4 shows a perspective view of the imaging system of FIGS. 3A and 3B.

FIG. 14A shows a diagrammatic partial view of a mouse in a sample chamber on the sample object stage of the imaging system of FIGS. 3A and 3B when an X-ray anatomical image, with an X-ray contrast agent providing contrast of the gastrointestinal tract of the subject, is acquired in accordance with the present invention.

FIG. 14B shows an x-ray anatomical image captured using the imaging system of FIG. 14A.

FIG. 15A shows a diagrammatic partial view of a mouse in a sample chamber on the sample object stage of the imaging system of FIGS. 3A and 1B when a near-infrared fluorescence image of the gastro-intestinal tract is acquired in accordance with the present invention.

FIG. 15B shows a near-infrared fluorescence image captured using the imaging system of FIG. 15A.

FIGS. 17A, 17B and 17C respectively show an anatomical X-ray image with an X-ray contrast agent providing contrast of the kidneys of the subject, a near-infrared fluorescence image of the kidneys of the subject, and a co-registered image of the anatomical X-ray image and the near-infrared fluorescence images of the kidneys of the subject, acquired in accordance with the method of the present invention.

DETAILED DESCRIPTION OF THE INVENTION

Figure 5A:
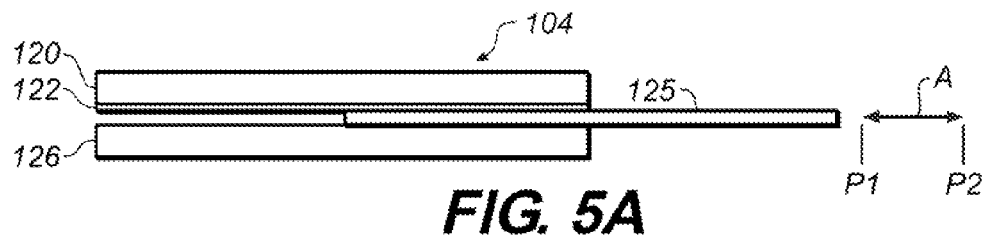
FIG. 5A shows a diagrammatic side view of the sample object stage, showing the relative movement of the phosphor plate relative to the sample object stage.

The following is a detailed description of the preferred embodiments of the invention, reference being made to the drawings in which the same reference numerals identify the same elements of structure in each of the several figures.

In the complex pharmaceutical analyses of small objects or subjects such as small animals and tissue samples, images are particularly enhanced by using different in-vivo imaging modalities. Using the known or current practices of bright-field, dark-field and radiographic imaging for the analysis of small objects or subjects such as a mouse can be expensive and may not provide the precision of co-registered images that is desired.

Using the method and apparatus of the present invention, precisely co-registered images can be obtained using x-ray and fluorescent, luminescent, or radioactive isotopic probes, individually or in combination, within an object such as a live animal or a tissue sample. The images can be localized and multiple images can be accurately overlaid onto the simple bright-field reflected image or anatomical x-ray image of the same animal within minutes of animal immobilization.

The method and apparatus of the present invention use the same imaging system to capture images using different modes of imaging, thereby enabling or simplifying multi-modal imaging. In addition, relative movement of imaging probes can be kinetically resolved over the time period that the animal is effectively immobilized, which can be tens of minutes. Alternatively, the same animal may be subject to repeated complete image analysis over a period of days or weeks required to assure completion of a pharmaceutical study, with the assurance that the precise anatomical frame of reference (particularly, the x-ray image) may be readily reproduced upon repositioning the object animal. The method of the present invention can be applied to other objects or complex systems, or both, subject to simple planar imaging methodologies. More particularly, using the imaging method of the present invention, an immobilized object can be imaged in several imaging modes without changing or moving the immobilized object. These acquired multi-modal images can then be merged to provide a co-registered image for analysis.

Imaging modes supported by the method of the present invention include: x-ray imaging, bright-field imaging, dark-field imaging (including luminescence imaging, fluorescence imaging) and radioactive isotope imaging. Images acquired in these modes can be merged in various combinations for analysis. For example, an x-ray image of the object can be merged with a near-infrared fluorescence image of the object to provide a new image for analysis.

The use of molecular imaging has engendered a need to co-register fluorescent and luminescent, or radioactive isotope signals with anatomical features of the animal or specimen. The type of imaging system particularly useful for the method and apparatus of the present invention utilizes a low energy X-ray source and phosphor screen to supplement the optical imaging modalities. An X-ray image provides a convenient anatomical map of musculoskeletal features, and is an orthogonal imaging modality that will not pollute optical signals emanating from the subject. While the skeleton provides the framework to spatially assign organs, X-ray contrast agents are used in the method of the invention to provide an effective means to delineate soft tissues that typically give poor contrast by X-ray. For example, many optical or radio-isotopic signals emanate from soft tissues like the kidneys, liver, and gastrointestinal tract during circulation and clearance. Thus, it is particularly important to identify and delineate these organ structures in an X-ray to provide anatomical co-registration of these signals.

An embodiment of the apparatus of the present invention, useful to practice the method of the invention, is now described with reference to FIGS. 3A, 3B, and 4. Imaging system 100 includes light source 12, optical compartment 14, a lens and camera system 18, and communication and computer control system 20 which can include computer monitor 22. As best shown in FIG. 3A, imaging system 100 includes an x-ray source 102 and a sample object stage or support member 104. An immobilized object, such as a mouse, is received on and supported by sample object stage 104 during use of system 100. Imaging system 100 further comprises epi-illumination, for example, using fiber optics 106, which directs conditioned light (of appropriate wavelength and divergence) toward sample object stage 104 to provide brightfield or fluorescent imaging. Sample object stage or support member 104 is disposed within a sample environment 108, which allows access to the object being imaged. Preferably, sample environment 108 is light-tight and fitted with light-locked gas ports (not illustrated) for environmental control. Such environmental control might be desirable for controlled x-ray imaging or for support of particular specimens. Environmental control enables practical x-ray contrast below 8 Kev (air absorption) and aids in life support for biological specimens. Imaging system 100 can include an access means/member 110 to provide convenient, safe and light-tight access to sample environment 108, such as a door, opening, labyrinth, and the like. Additionally, sample environment 108 is preferably adapted to provide atmospheric control for sample maintenance or soft x-ray transmission (e.g., temperature/humidity/alternative gases and the like). Imaging system 100 can be a unitary system. Alternatively, imaging system 100 can be a modular unit adapted to be used or mated with electronic imaging system such as electronic imaging system 10.

Figure 5B:
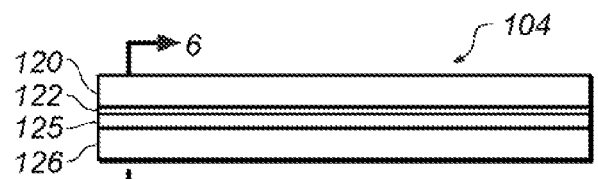
FIG. 5B shows a diagrammatic side view of the sample object stage in the first imaging position P1 wherein the phosphor plate is disposed proximate the sample object stage.
Figure 5C:
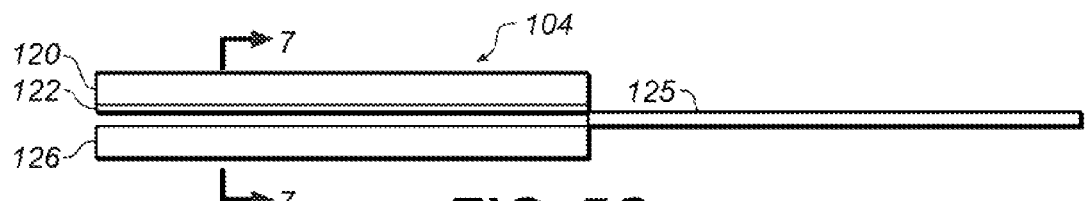
FIG. 5C shows a diagrammatic side view of the sample object stage in the second imaging position P2 wherein the phosphor plate is not proximate the sample object stage.
Figure 6:
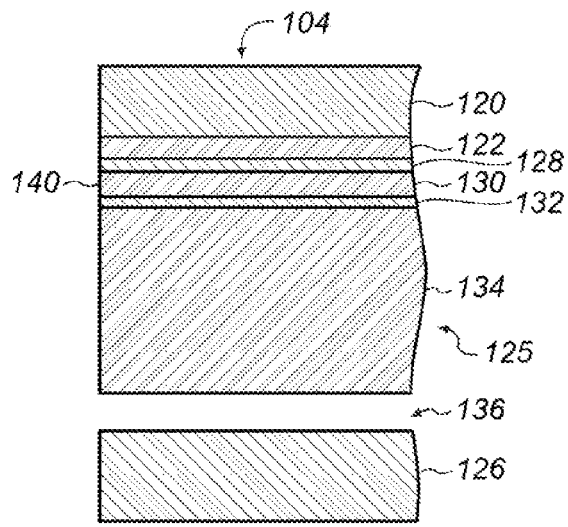
FIG. 6 shows an enlarged, fragmentary sectional view taken along line 6-6 of FIG. 5B.
Figure 7:
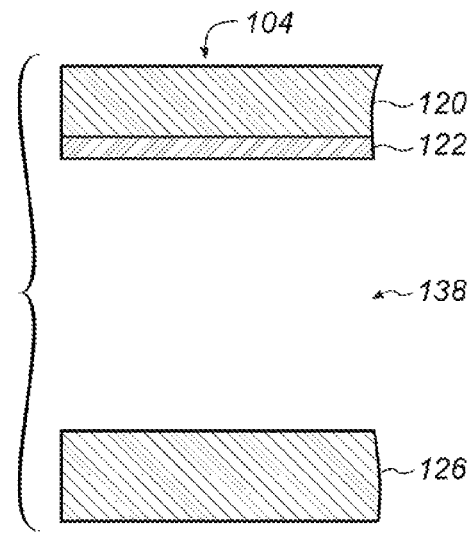
FIG. 7 shows an enlarged, fragmentary sectional view taken along line 7-7 of FIG. 5C.

FIGS. 5-7 more particularly illustrate elements of sample object stage 104 and an optical interface relative with the focal plane of camera and lens system 18. FIG. 5A shows a diagrammatic side view of sample object stage 104 showing the relative movement of a movable phosphor plate 125 according to the invention relative to the sample object stage. FIG. 5B shows a diagrammatic side view of the sample object stage in a first imaging position P1 wherein phosphor plate 125 is disposed proximate the sample object stage and positioned for imaging light from a phosphor layer 132, as shown in FIG. 6. FIG. 5C shows a diagrammatic side view of the sample object stage in the second imaging position P2 wherein phosphor plate 125 has been withdrawn to a position that is not proximate the sample object stage. FIG. 6 shows an enlarged, fragmentary sectional view taken along line 6-6 of FIG. 5B, which corresponds with the first imaging position P1. FIG. 7 shows an enlarged, fragmentary sectional view taken along line 7-7 of FIG. 5C, which corresponds with the second imaging position P2.

Continuing with regard to FIGS. 6 and 7, sample object stage 104 includes a support member made up from an open frame 120 to support and stretch a thin plastic support sheet 122. Support sheet 122 is selected so as to support the weight of a sample or object to be imaged and is made from a material that is optically clear and free of significant interfering fluorescence. Phosphor plate 125 is mounted for motion toward and away from sample object stage 104. While those skilled in the art might recognize other configurations, in a preferred embodiment, phosphor plate 125 is mounted for translation to provide slidable motion (in the direction of arrow A in FIG. 5A) relative to frame 120, beneath the sample, in intimate contact with support sheet 122. Such motion can be accomplished using methods known to those skilled in the art, for example, frame 100 and phosphor plate 125 can be disposed on rails supported by a surface of an optical platen 126. As will be more particularly described below, in first imaging position P1, phosphor layer 130 in phosphor plate 125 is in overlapping arrangement with sample object stage 104 (FIG. 6) when an x-ray image of the object is captured. In second imaging position P2, phosphor plate 125 is translated or moved away from sample object stage 104 (FIG. 7) for capture of an image of the object such that phosphor plate 125 is not imaged when an image of the object is captured in second imaging position P2.

FIG. 6 provides an enlarged view of sample object stage 104 including phosphor plate 125 to more particularly show a focal plane. Sample support sheet 122 preferably comprises Mylar or polycarbonate and has a nominal thickness of about 0.1 mm. A protective layer 128 (for example, reflective Mylar) of about 0.025 mm is provided on phosphor layer 130 to protect the surfaces of layer 130 during movement of phosphor plate 125. Protective layer 128 promotes or increases the image-forming light output. In a preferred embodiment, protective layer 128 is reflective so as to prevent object reflection back into the image-forming screen, reducing confusing of the ionizing radiation image.

Phosphor layer 130 functions to transduce ionizing radiation to visible light practically managed by lens and camera system 18 (such as a CCD camera). Phosphor layer 130 can have a thickness ranging from about 0.01 mm to about 0.1 mm, depending upon the application (i.e., soft x-ray, gamma-ray or fast electron imaging). On the underside of phosphor layer 130, as illustrated, an optical layer 132 is provided for conditioning emitted light from phosphor layer 130. Optical layer 132 can have a thickness in the range of less than about 0.001 mm. Particular information about phosphor layer 130 and optical layer 132 are disclosed in U.S. Pat. No. 6,444,988 (Vizard), commonly assigned and incorporated herein by reference. A supporting glass plate 134 is provided. Glass plate 134 is spaced at a suitable mechanical clearance from optical platen 126, for example, by an air gap or void 136. In one embodiment, the surfaces of clear optical media (e.g., a lower surface of glass plate 134 and both surfaces of optical platen 126) are subject to anti-reflective coating to minimize reflections that may confuse the image of the object. FIG. 7 provides an expanded view of sample object stage 13 including wherein phosphor plate 125 is removed (i.e., taken along line 7-7 of FIG. 5C). Shown in FIG. 7 are frame 120, sample support sheet 122, an air gap/void 138 (since phosphor plate 125 is removed), and optical platen 126.

Figure 8:
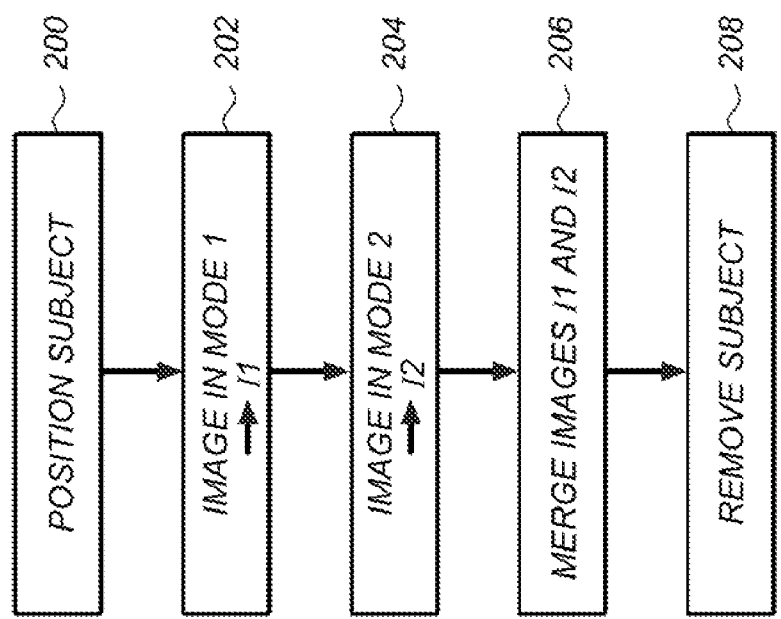
FIG. 8 shows a work flow diagram in accordance with the mode of operation of the system of FIGS. 1 to 7.

Referring now to FIG. 8, in operation, in Step 200 an object (such as a small animal) is immobilized on sample object stage 104. An operator configures system 100 for imaging in a first mode, and in Step 202 an image of the object is captured using lens and camera system 18 in the first mode. System 18 converts the light image into an electronic image which can be digitized. This digitized image is referred to as Image1 or I1. The digitized image can be displayed on the display device, stored in memory, transmitted to a remote location, processed to enhance the image, and/or used to print a permanent copy of the image. The object remains immobilized on sample object stage 104; no change in the position/location of the object is made. The operator configures system 100 for imaging in Step 204 and an image of the object is captured using lens and camera system 18 in a second mode. The resulting digitized image is referred to as Image2 or I2. Since the position of the object was not moved or changed during the capture of the images, both Image1 and Image2 can readily be merged or superimposed in Step 206, using methods known to those skilled in the art, such that the two images are co-registered. As such, a third image can be generated comprising Image1 and Image2. In Step 208, the animal is removed from the object stage.

As indicated above, system 100 can be configured in several modes, including: x-ray imaging, bright-field imaging, dark-field imaging (including luminescence imaging, fluorescence imaging) and radioactive isotope imaging. To configure system 100 for x-ray imaging or isotope imaging, phosphor plate 125 is moved to position P1 in optical registration with sample object stage 104 (as shown in FIGS. 5B and 6). For an x-ray image, x-ray source 102 is employed when capturing the image of the immobilized object. To configure system 100 for bright-field imaging or dark-field imaging (including luminescence imaging and fluorescence imaging) without moving the immobilized object and the support member or object stage, phosphor plate 125 is moved to position P2, out of optical registration with sample object stage 104 (as shown in FIGS. 5C and 7), and an image of the immobilized object is appropriately captured. The object is immobilized on sample object stage 104, and light emitted from the object (usually diffusive within the turbid constituents of a solid object) is projected to the object surface, which intimately bears upon the upper surface of sample support sheet 122.

For the purpose of optical imaging, the object surface is defined by a refractive boundary (e.g., the skin of an animal) that delineates the interior of the object (usually a heterogeneous, turbid media of higher index of refraction) and air. Light emanating from within an object (e.g., luminescent or transmitted) projects to the surface from which it scatters, defining the light that may be productively managed to create an image of the object. Conversely, light may be provided from beneath optical platen 126 and scattered from the object surface, thereby providing reflective light for imaging the same object. For optical imaging, the definition of the object boundary may be moderated by matching the refractive index of the object boundary to support sheet 122 by introducing an index-matching fluid (e.g., water). The depth to which good focus can be achieved in optical imaging is dependent on minimizing the surface scatter of the object, and methods such as index matching and increasing wavelength (e.g., near-infrared imaging) are well known in the art.

The emitted sample light can arise from luminescence, fluorescence, or reflection, and the focal plane of the lens can be adjusted to the elevation of object surface. Alternatively, the "light" can be ionizing radiation passing through or emitted from the object, or passing into the phosphor and forming an image. Soft x-rays, consistent with thin objects or small animals, project an image through the diffusive phosphor onto the optical boundary, adding the depth of the (more than about 0.02 mm) to the depth of focus. More significant is the focal distance contributed by the phosphor support plate 134, which may be fractional millimeters, depending upon the thickness and index of the glass or plastic. The fractional-millimeter elevation of the best focal plane contributed by the phosphor support can provide a better coincidence between the phosphor focal plane and the focal plane used for optical imaging. For near-infrared optical imaging, the preferred/best focal plane may be located at millimeter depths into a nominally turbid object. The phosphor support plate 134 can be thicker to maximize the coincidence of the optical and phosphor imaging planes. Those skilled in the art will recognize how to tune the materials of the present invention to optimally co-locate the preferred optical and phosphor imaging planes. Currently described materials may be practically assembled to assure multi-modal focal plane co-location to accommodate the demands of a fast lens system.

Appropriately fast lens systems for dark-field and x-ray imaging applications will likely have sub-millimeter focal depths, necessitating the above considerations. Accordingly, for a particular embodiment, it may be desirable for multiple optical elements to enable the location of a common focal plane shared by differing modes of imaging.

Emitted gamma rays from a thick object (such as 99Tc emission from an animal organ) are distributed over the plane of the phosphor, diffusing the image by millimeters, and an appropriately thick phosphor layer (about 0.1 mm) may be preferred for increased detection efficiency. Consequently, the location of the focal plane at the supporting sheet is not critical to the resolution of the radio isotopic image. Better resolution and more precise planar projection of the emitting isotope can be achieved by gamma-ray collimation. Collimators of millimeter-resolution are available and capable of projecting isotopic location to millimeter resolution at the focal plane of the phosphor in the present invention.

Of particular relevance to the operation of the present invention is the thickness of the layers in the focal plane of the lens. For example, fast lenses, (which are essential elements for the practice of imaging low-light emissions) will have a focal depth of focus of about 0.5 mm for very fast lenses. For good resolution of objects of interest, less than about 0.2 mm of spatial resolution is desirable, and a megapixel CCD camera (cooled) imaging at 100 mm field is suitable. Generally, more resolution is desirable.

Precision registration of the multi-modal image can be accomplished using methods known to those skilled in the art. By placing the object on a thin, stretched optical support that allows phosphor plate 125 to be removed without displacement of the object, co-registered optical imaging is enabled by the same lens and camera system using epi-illumination methodologies at a sufficiently similar focal plane.

Figure 9A:
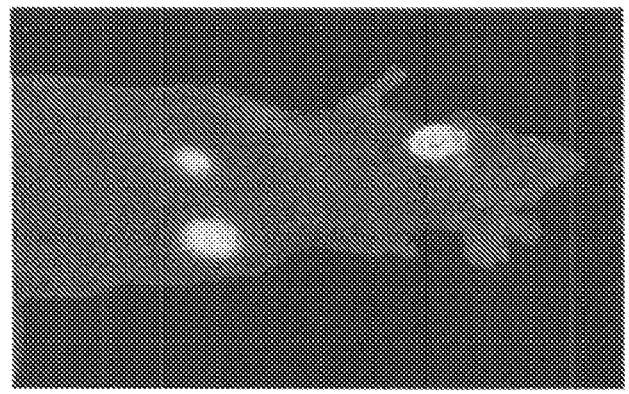
FIG. 9A shows a first image of an immobilized object in a first, fluorescence imaging mode.
Figure 9B:
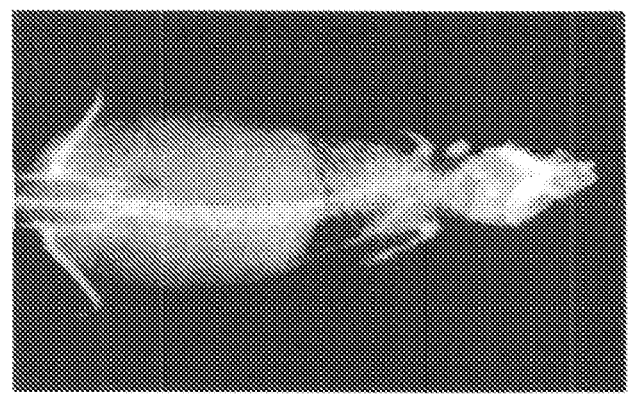
FIG. 9B shows a second image of the immobilized object of FIG. 9A in a second, x-ray imaging mode.
Figure 9C:
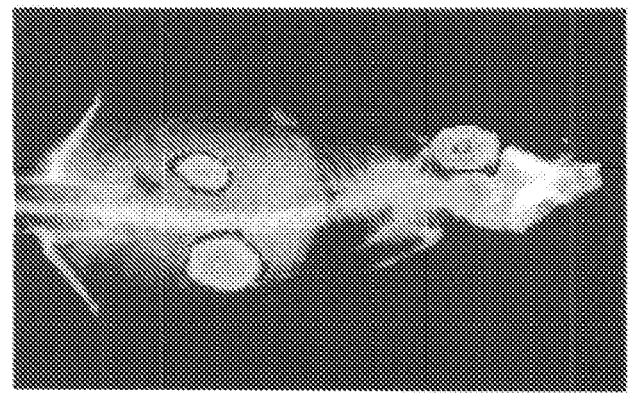
FIG. 9C shows an image generated by thresholding the image of FIG. 9A and then merging that image with the image of FIG. 9B.

Examples are now provided. FIGS. 9A-9C show images captured using the apparatus and the method of the present invention. A mouse was immobilized on sample object stage 104 (step 200 of FIG. 8) of system 100. System 100 was first configured for near-infrared fluorescence imaging wherein phosphor plate 125 is removed from co-registration with frame 100. A first image was captured and is displayed in FIG. 9A (step 202 of FIG. 8). Next, system 100 was configured for x-ray imaging wherein phosphor plate 125 is placed in co-registration with frame 100. A second image was captured and is displayed in FIG. 9B (step 204 of FIG. 8). Using methods known to those skilled in the art, the image of FIG. 9A was thresholded to make transparent those regions with pixel intensity values less than the threshold value and then the thresholded image was merged with the image of FIG. 9B in step 206 of FIG. 8; and the merged image is displayed in FIG. 9C. Note that the fluorescent signals superimposed on the anatomical reference clarify the assignment of signal to the bladder and an expected tumor in the neck area of this illustrated experimental mouse. It is noted that the first and/or second image can be enhanced using known image processing methods/means prior to be merged together. Alternatively, the merged image can be enhanced using known image processing methods/means. Often, false color is used to distinguish fluorescent signal from gray-scale x-rays in a merged image.

Figure 10C:
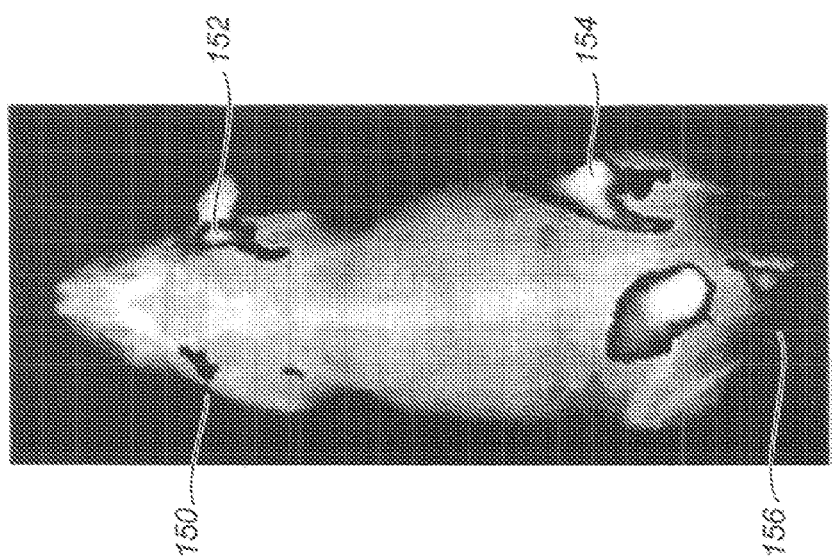
FIG. 10C shows an image generated by thresholding the image of FIG. 10A and then merging that image with the image of FIG. 10B.
Figure 10B:
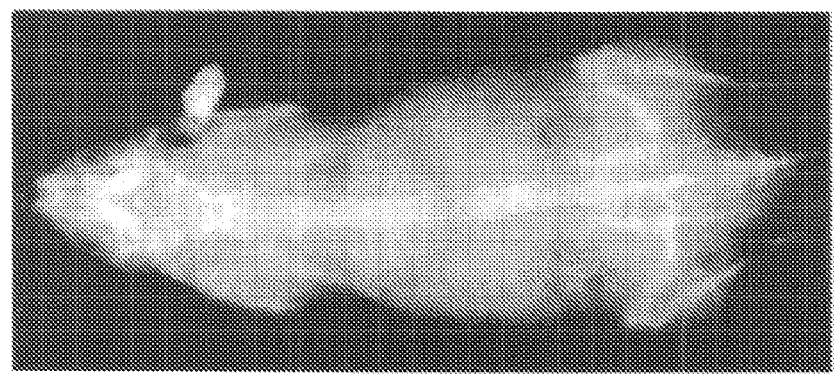
FIG. 10B shows a second image of the immobilized object of FIG. 10A in a second, x-ray imaging mode.
Figure 10A:
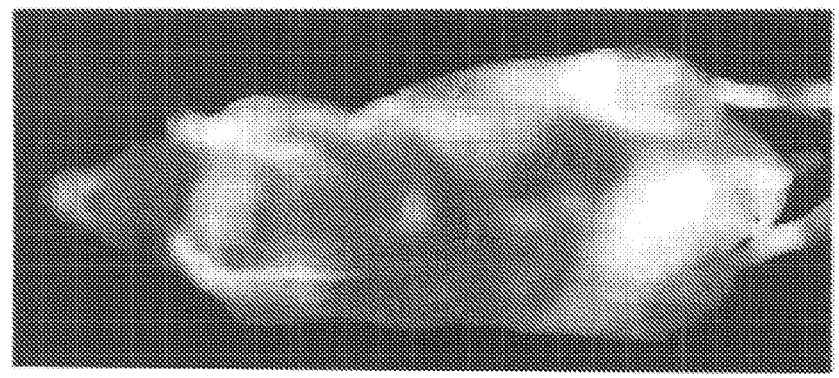
FIG. 10A shows a first image of an immobilized object in a first, fluorescence imaging mode.

FIGS. 10A-10C provide a further example using an apparatus suitable for use in accordance with the method of the present invention. FIG. 10A is a near-infrared fluorescence image of a mouse while FIG. 10B is an x-ray image of the same immobilized mouse. Using methods known to those skilled in the art, the first and second images were merged in the manner previously described and the merged image is displayed in FIG. 10C. Prior to being merged, the first and second images were contrasted, using methods known to those skilled in the art. This processing allows particular areas of the mouse to be visually enhanced for diagnostic purposes.

For example, areas 150, 152, and 156 are potential secondary early detection sites, and area 154 shows the primary tumor injection site at the knee.

Figure 11C:
FIG. 11C shows an image generated by thresholding the image of FIG. 11A and then merging that image with the image of FIG. 11B.
Figure 11B:
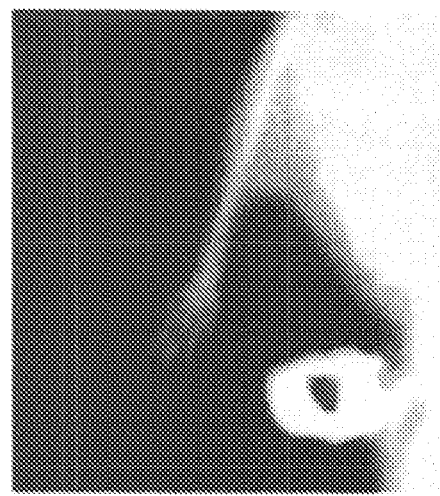
FIG. 11B shows a second image of the immobilized object of FIG. 11A in a second, x-ray imaging mode.
Figure 11A:
FIG. 11A shows a first image of an immobilized object in a first, fluorescence imaging mode.

FIGS. 11A-11C provide yet a further example using an apparatus suitable for use in accordance with the method of the present invention. FIG. 11A is a near-infrared fluorescence image of a mouse wrist while FIG. 11B is an x-ray image of the same immobilized mouse wrist. Using methods known to those skilled in the art, the first and second images were merged in the manner previously described and the merged image is displayed in FIG. 11C. The merged image provides a diagnostic image for viewing a potential secondary tumor site. Note that this image set clearly demonstrates the precision with which the apparatus of FIGS. 1 to 8 enables the co-location of images of objects from differing imaging modes. The maximum fluorescent signal emanating from a pre-metastatic tumor on the radius (arm-bone) tip at the wrist is within about 0.1 mm of the suspect lesion subsequently identified by microscopic histology.

Figure 12:
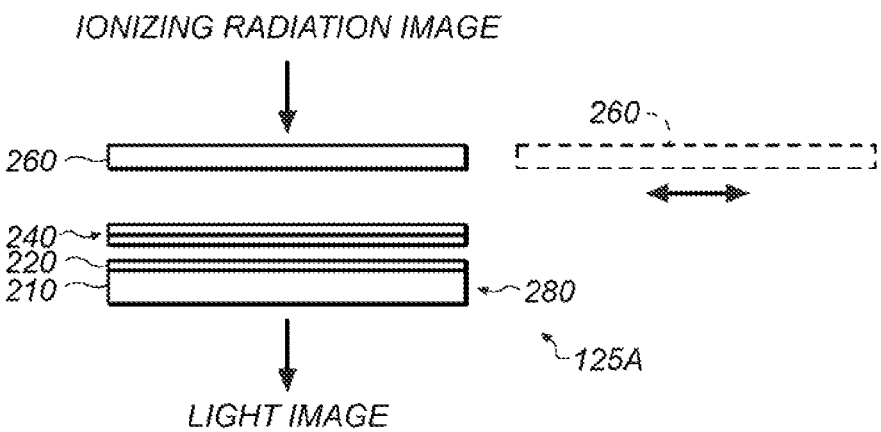
FIG. 12 is a diagrammatic view of a suitable phosphor plate for use with the apparatus suitable for practice of the method of the present invention.

A phosphor plate suitable for use with the method of the present invention is disclosed in U.S. Pat. No. 6,444,988 (Vizard), commonly assigned and incorporated herein by reference. A phosphor plate as described in Vizard is shown in FIG. 12. A suitable phosphor plate 125A for use with the apparatus and the method of the present invention includes a transparent support 210 (such as glass) upon which is coated an interference filter 220 which is a multicoated short-pass filter designed to transmit light at a specified wavelength (and below) and reflect light above that wavelength. Plate 125A also includes a thin phosphor layer 240 and a removable thick phosphor layer 260. Thin phosphor layer 240 is used for high resolution imaging applications of ionizing radiation or for very low energy (self-attenuating) ionizing radiation such as low-energy electrons or beta particles. Thick phosphor layer 260 is used for high-energy ionizing radiation that freely penetrates the phosphor. Thick phosphor layer 260 is removable and is shown in FIG. 12 overlaying thin phosphor layer 240. Layer 260 is removable to the position shown in dashed lines out of contact with layer 240.

The phosphor preferably used in phosphor layers 240 and 260 is Gadolinium Oxysulfide Terbium whose strong monochromatic line output (544-548 nanometers (NM)) is ideal for co-application with interference optics. This phosphor has technical superiority regarding linear dynamic range of output, sufficiently "live" or prompt emission and time reciprocity, and intrascenic dynamic range which exceed other phosphors and capture media. This phosphor layer preferably has a nominal thickness of 10-30 micrometers ($\mu$m) at 5-20 grams/square foot (g/ft$^2$) of phosphor coverage, optimally absorbing 10-30 Kev x-rays. Thick phosphor layer 260 has a nominal thickness of 100 $\mu$m at 80 g/ft$^2$ of phosphor coverage.

The duplex phosphor layers impart flexibility of usage for which the thick phosphor layer 260 may be removed to enhance the spatial resolution of the image. Thin phosphor layer 240 intimately contacts filter 220, whereas thick phosphor layer 260 may be alternatively placed on thin phosphor layer 240. Interference filter 220 transmits light at 551 NM and below and reflects light above that wavelength. Filter 220 comprises layers of Zinc Sulfide-Cryolite that exhibits a large reduction in cutoff wavelength with increasing angle of incidence. The filter has a high transmission at 540-551 NM to assure good transmission of 540-548 NM transmission of the GOS phosphor. The filter also has a sharp short-pass cut-off at about 553 NM, that blue shifts at about 0.6 NM per angular degree of incidence to optimize optical gain. Glass support 210 should be reasonably flat, clear, and free of severe defects. The thickness of support 210 can be 2 millimeters. The opposite side 280 of glass support 210 is coated with an anti-reflective layer (such as Magnesium Fluoride, green optimized) to increase transmittance and reduce optical artifacts to ensure that the large dynamic range of the phosphor emittance is captured.

Figure 13:
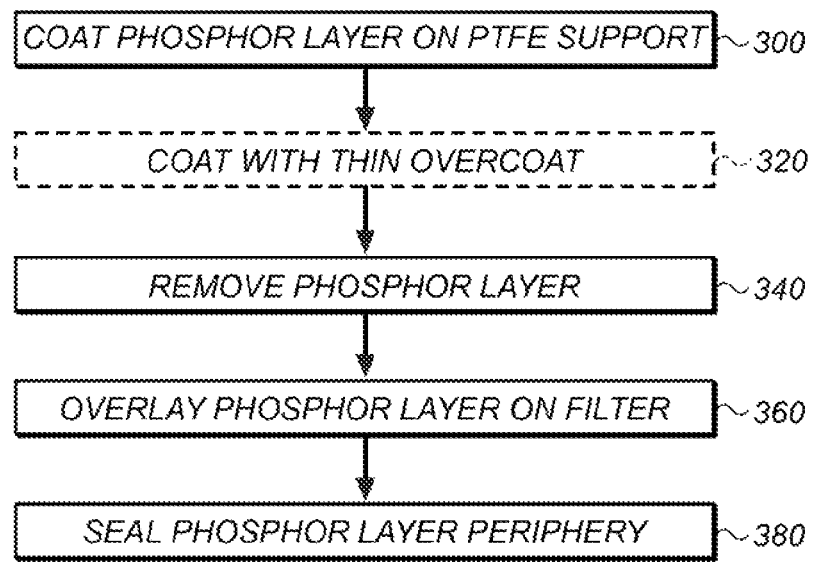
FIG. 13 is a flow diagram of a method for making a phosphor plate of FIG. 12.

Referring now to FIG. 13, there is shown a method of producing phosphor layer 240. In Step 300, a mixture of GOS:Tb in a binder is coated on a polytetrafluoroethylene (PTFE) support. The PTFE support enables release of the coated phosphor layer from the PTFE support and subsequent use of the phosphor layer without support, since conventional supporting materials are an optical burden to screen performance. For the thin phosphor layer 240, in Step 320 an ultra thin (about 0.5 g/ft$^2$, 0.5 $\mu$m thick) layer of cellulose acetate overcoat can be applied to offer improved handling characteristics of the thin phosphor layer and to provide greater environmental protection to the underlying optical filter. In Step 340, the phosphor layer is removed from the PFTE support. The thin phosphor layer overcoated side is overlayed on interference filter 220 in Step 360. Clean assembly of the thin phosphor layer 240 and filter 220 assures an optical boundary that optimizes management of screen light output into the camera of the lens/camera system. Optical coupling of layer 240 and filter 220 is not necessary, since performance reduction may result. In Step 380, layer 240 can be sealed around its periphery and around the periphery of filter 220 for mechanical stability and further protection of the critical optical boundary against environmental (e.g., moisture) intrusion.

Advantages of the method of the present invention include: anatomical localization of molecular imaging agent signals in small animals, organs, and tissues; precise co-registration of anatomical x-ray images with optical molecular and radio isotopic images using one system; improved understanding of imaging agent's biodistribution through combined use of time lapse molecular imaging with x-ray imaging; and simple switching between multi-wavelength fluorescence, luminescence, radio-isotopic, and x-ray imaging modalities without moving the object/sample.

Reference is made to the following commonly assigned, copending U.S. patent applications: Ser. No. 12/381,599 filed Mar. 13, 2009 by Feke et al, entitled METHOD FOR REPRODUCING THE SPATIAL ORIENTATION OF AN IMMOBILIZED SUBJECT IN A MULTI-MODAL IMAGING SYSTEM; and Ser. No. 12/475,623 filed Jun. 1, 2009 by Feke et al, entitled TORSIONAL SUPPORT APPARATUS AND METHOD FOR CRANIOCAUDAL ROTATION OF ANIMALS, the disclosures of both of which are incorporated by reference into this specification.

FIGS. 14A, 14B, 15A and 15B show a diagrammatic partial view of the sample stage 104 (a transparent tube in this instance) of the imaging system 100 of FIGS. 3A and 3B where the subject mouse 112 is positioned in a chamber 113 and administered immobilizing anesthesia through a respiratory device 114 connected to an outside source via a tube 115 which enters the sample environment 108 via the light-locked gas ports. A rotational mechanism 116 may be provided for adjusting the rotational position of the mouse about its craniocaudal axis. A translational mechanism 117 may be provided to adjust the axial location of the mouse relative to source 102 and fiber optics 106. Further details of the structure shown in these figures are disclosed in the first application of Feke et al, mentioned in the preceding paragraph. An X-ray anatomical image 140 and a near-infrared fluorescence image 142 are acquired of the gastrointestinal tract of the immobilized subject mouse 112. Images 140, 142 are shown side by side in FIGS. 16A and 16B.

In a preferred embodiment of the present invention, referring to FIGS. 14A and 14B, an X-ray image 140 provides a convenient anatomical map of musculoskeletal features of the subject mouse 112. The X-ray image 140 is an orthogonal imaging modality that will not pollute optical signals emanating from the subject. While the skeleton provides the framework to spatially assign organs, X-ray contrast agents may be administered to the mouse in accordance with the invention to provide an effective means to delineate tissues that typically give poor contrast by X-ray.

Figure 21:
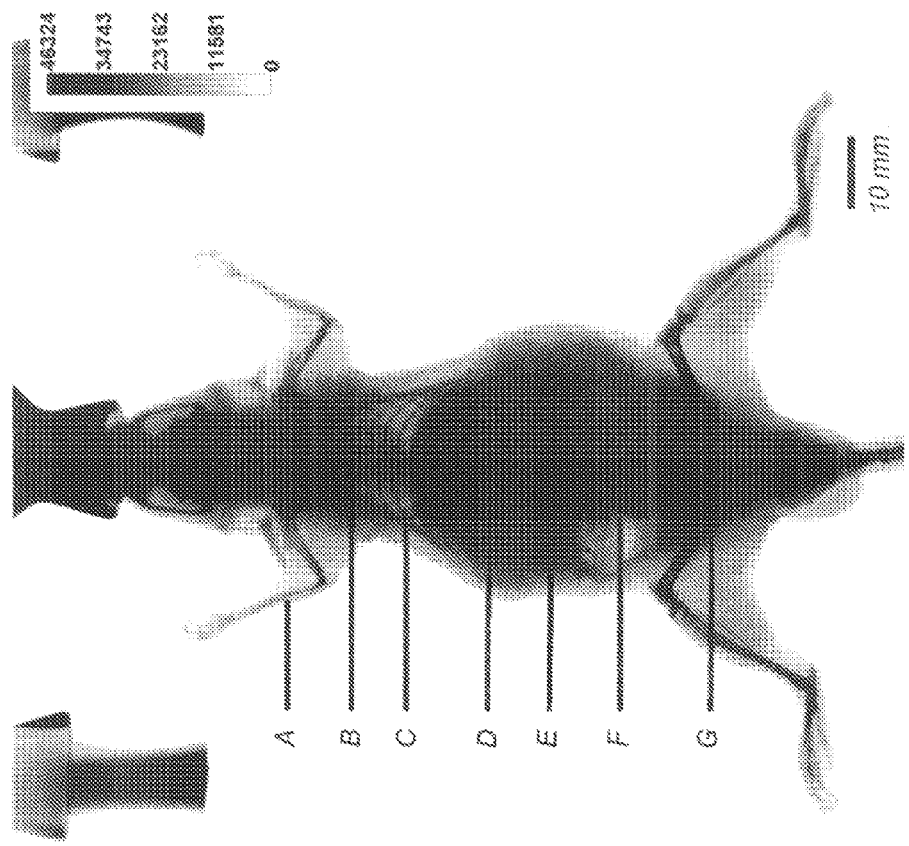
FIG. 21 shows an anatomical X-ray image of a mouse in a sample chamber on the sample object stage of the imaging system of FIGS. 3A and 3B.

FIG. 21 shows an anatomical X-ray image of a mouse in the sample chamber on the sample object stage of the imaging system of FIGS. 3A and 1B. Labels refer to regions A: Bones/Joints, B: Heart, C: Lungs, D: Liver, E: Kidneys, F: GI Tract, and G: Bladder. Since bones are dense structures they absorb X-rays and appear dark. One can immediately note the fine structure in bones that are sub-millimeter in scale, like the rib cage and fibia bones in the leg. Many disease models involving the skeleton may be non-invasively studied using such images. These include bone growth and damage in response to environmental or physical inputs. Furthermore, subtle changes in bone density may also be measured. While bones are dense and provide positive contrast that appears black, air is obviously of low density and absorbs very little X-ray radiation. Thus, locations in an animal that contain gases give contrast toward the white end of the intensity spectrum shown in FIG. 21. One area in which air is plentiful is in the lungs (FIG. 21 region C). In fact, the rib cage is often considered a cavern of air due to the presence of the lungs, which appear as a triangular pattern on each half of the rib cage. Incidentally, another area in which gas tends to build up and give negative contrast on X-ray is in the bowels (FIG. 21 region F). Nevertheless, the air cavern of the rib cage is home to another important organ: the heart (FIG. 21 region B). Since the tissue comprising the heart has higher density than air, it gives positive (dark) contrast in comparison to the lungs. Indeed, since this organ is effectively surrounded by air from the lungs, it is often described as a "heart shadow" in the rib cage. The size of the heart shadow may be measured as it expands into the lung area. If its size increases too much, it is an indication of pulmonary edema, a condition in which the heart fills with liquid and expands to unsafe levels. Pulmonary edema has been measured and studied in rat models of heart disease. While the heart and lungs are soft tissue systems that are readily observed by X-ray, other organs possess little innate contrast to permit their imaging and require an alternate strategy. Organs like the stomach, gastrointestinal tract, kidneys, bladder and liver give little to no contrast during X-ray imaging. FIG. 21 regions D-F shows the lack of discernable contrast from each of these various tissue systems in the abdomen. However, through the use of x-ray contrast agents in accordance with the present invention, these organs can be delineated and studied in a non-invasive fashion using the X-ray modality. Molecules that incorporate atoms with exceptional X-ray absorption properties are typically utilized as contrast agents. Barium and iodine meet this criterion and are two of the most widely used atomic components of X-ray contrast agents. Indeed, both of these reagents have been utilized in the clinic for decades to perform gastric and heart perfusion imaging, among others. X-ray contrast agents effectively absorb X-ray irradiation, thus providing contrast in the organs in which they reside. Different X-ray contrast agents may be chosen depending on the organ to be imaged. For example, barium sulfate may be administered orally to the subject to view its stomach and gastrointestinal tract as shown in images 140 and 142 of FIGS. 14B and 16A. Iodinated contrast agents may be used intravenously to image the kidneys of the animal under study as shown in images 144 and 146 of FIG. 17. Other agents like gold nanoparticles may be used to add X-ray contrast to the liver, kidneys, or tumors.

The x-ray contrast agent may be administered at various time points in an imaging study to assign and delineate organs using X-ray imaging. A researcher will use that anatomical information to determine the contribution of fluorescent or luminescent signal emanating from that organ at that time point. For example as shown by the images in FIGS. 17A, 17B and 17C, a researcher may administer a fluorescent probe into an animal at time zero. At this and subsequent time points, the X-ray contrast agent may be given to the subject. A fluorescence image 146 is then acquired to capture signal from the original fluorescence probe as shown in FIG. 17B, and is immediately followed by an X-ray image 144 to view the organs as shown in FIG. 17A. In a final step, the images are then overlaid, or combined, to determine co-localization of the fluorescent signal to the organ of interest as shown in image 148 of FIG. 17C. Alternatively, the fluorescence imaging probe and the x-ray contrast agent may be administered to the mouse essentially simultaneously.

Referring now the workflow shown in FIG. 18 and FIGS. 17, 19 and 20, in Step 400 the optical imaging agent and X-ray contrast agent are introduced into the subject 112 as per the experimenter's protocol. In Step 410, the subject mouse 112 is placed on the object stage 104. The anatomical X-ray image 144 and near-infrared fluorescence image 146 are acquired in Step 420 and a co-registered image 148 of the anatomical X-ray image 144 and near-infrared fluorescence image 146 shown FIG. 17 is created in Step 430.

Figure 16B:
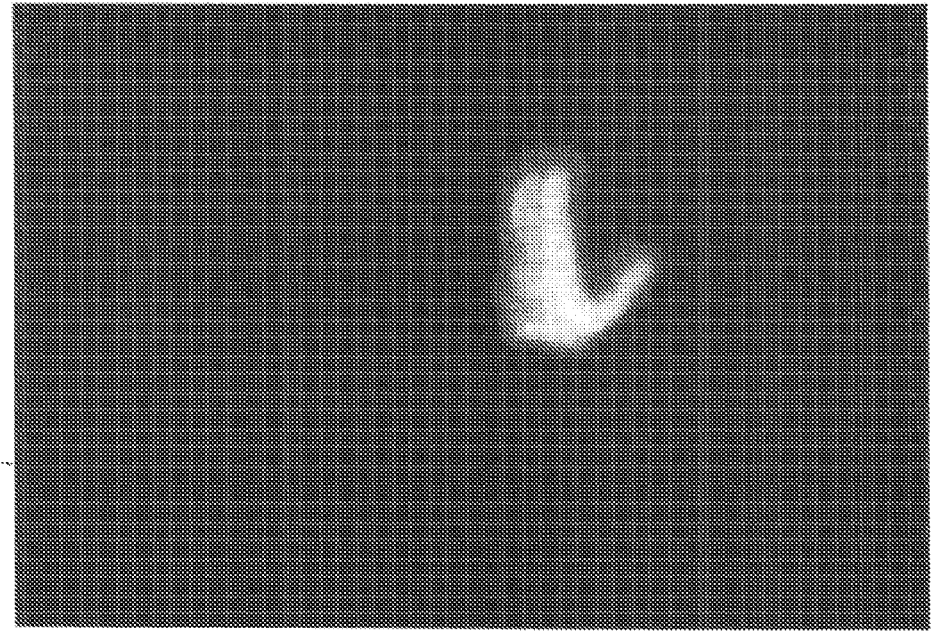
FIGS. 16A and 16B respectively show an anatomical X-ray image and a near-infrared fluorescence image of the gastro-intestinal tract of a subject acquired in accordance with the method of the present invention.
Figure 16A:
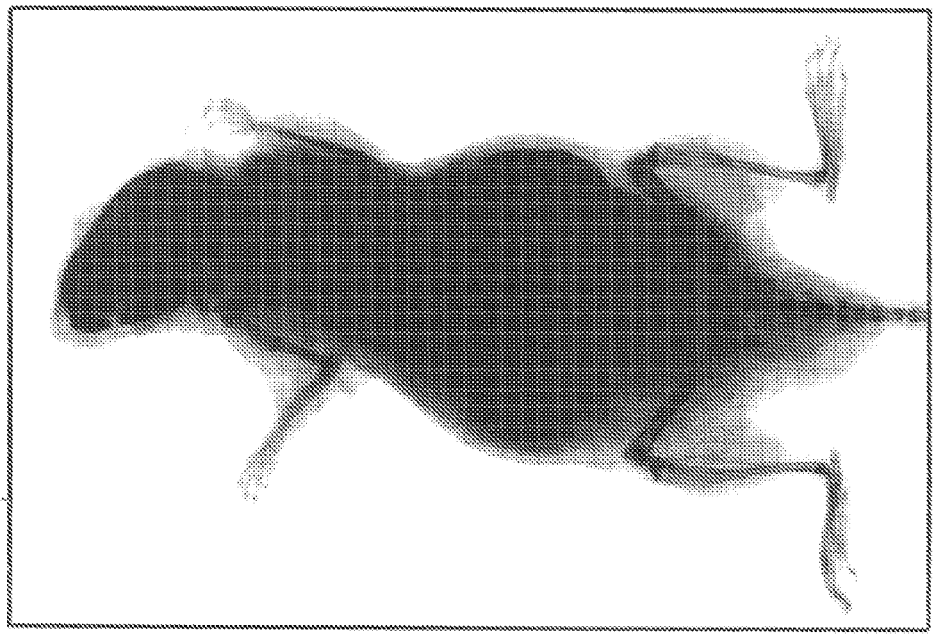
Figure 18:
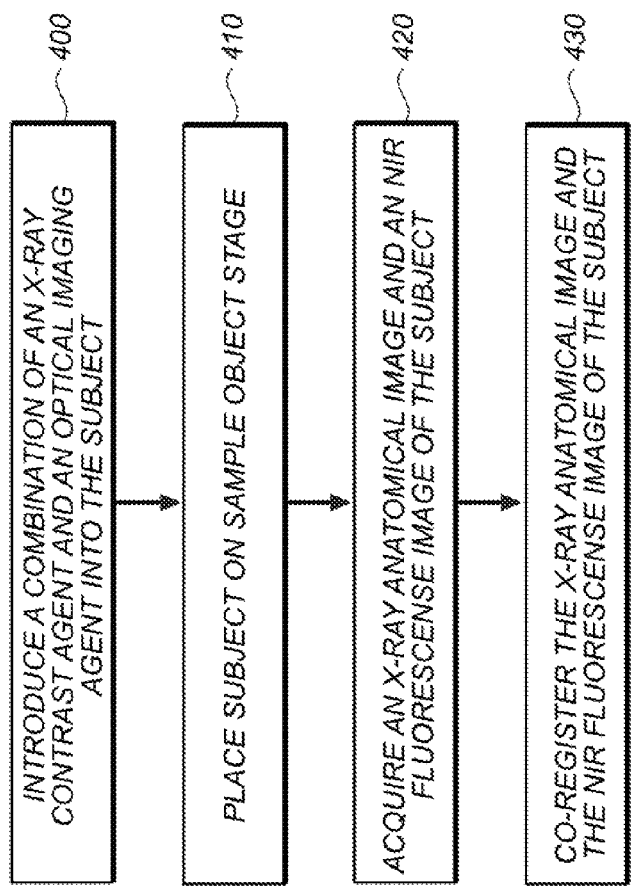
FIG. 18 shows a workflow diagram in accordance with a method of the present invention.
Figure 19:
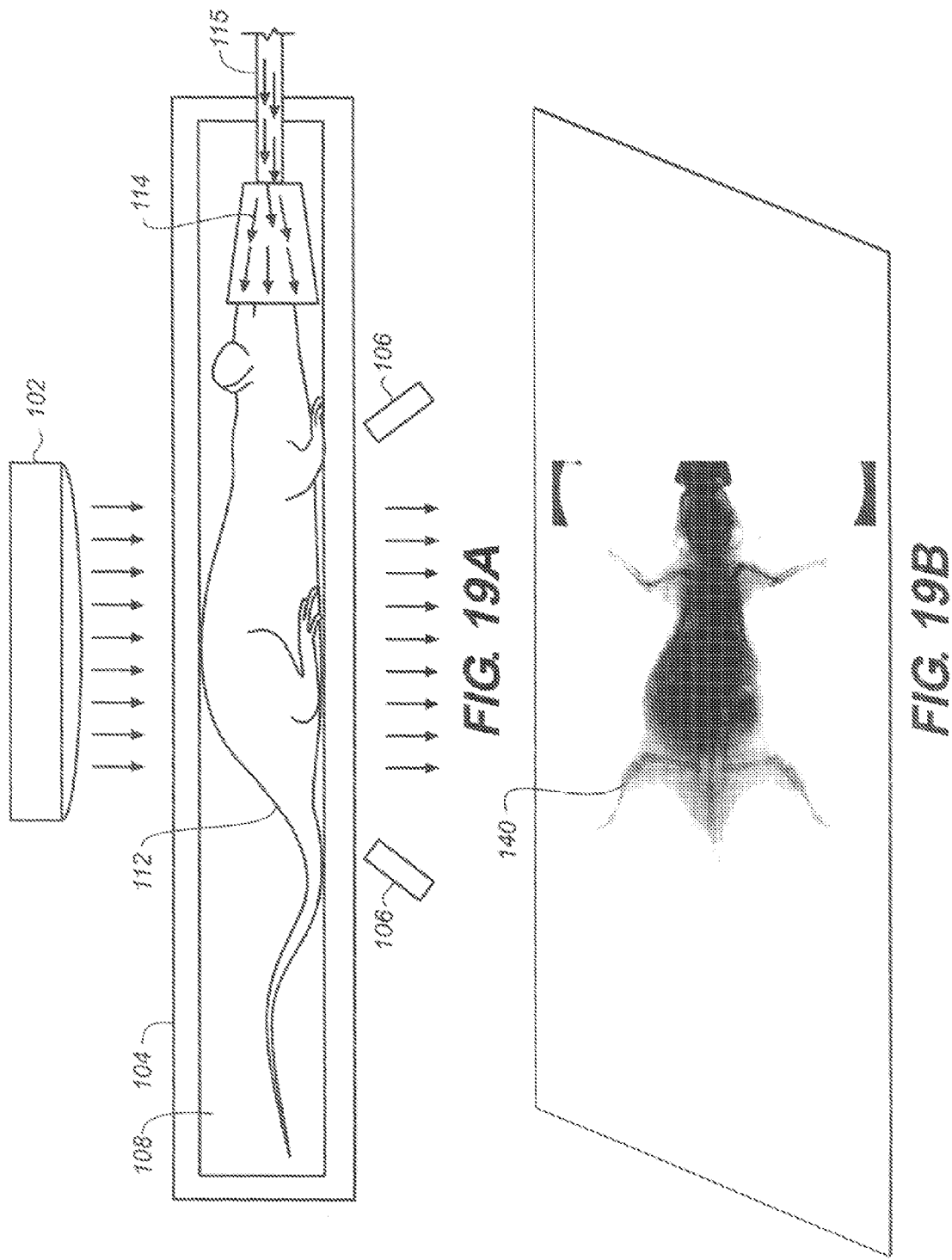
FIG. 19A shows a diagrammatic partial view of a mouse in a sample chamber on the sample object stage of the imaging system of FIGS. 3A and 3B when an X-ray anatomical image, with an X-ray contrast agent providing contrast of the kidneys of the subject, is acquired in accordance with the present invention.
FIG. 19B shows an x-ray anatomical image captured using the system of FIG. 19A.
Figure 20:
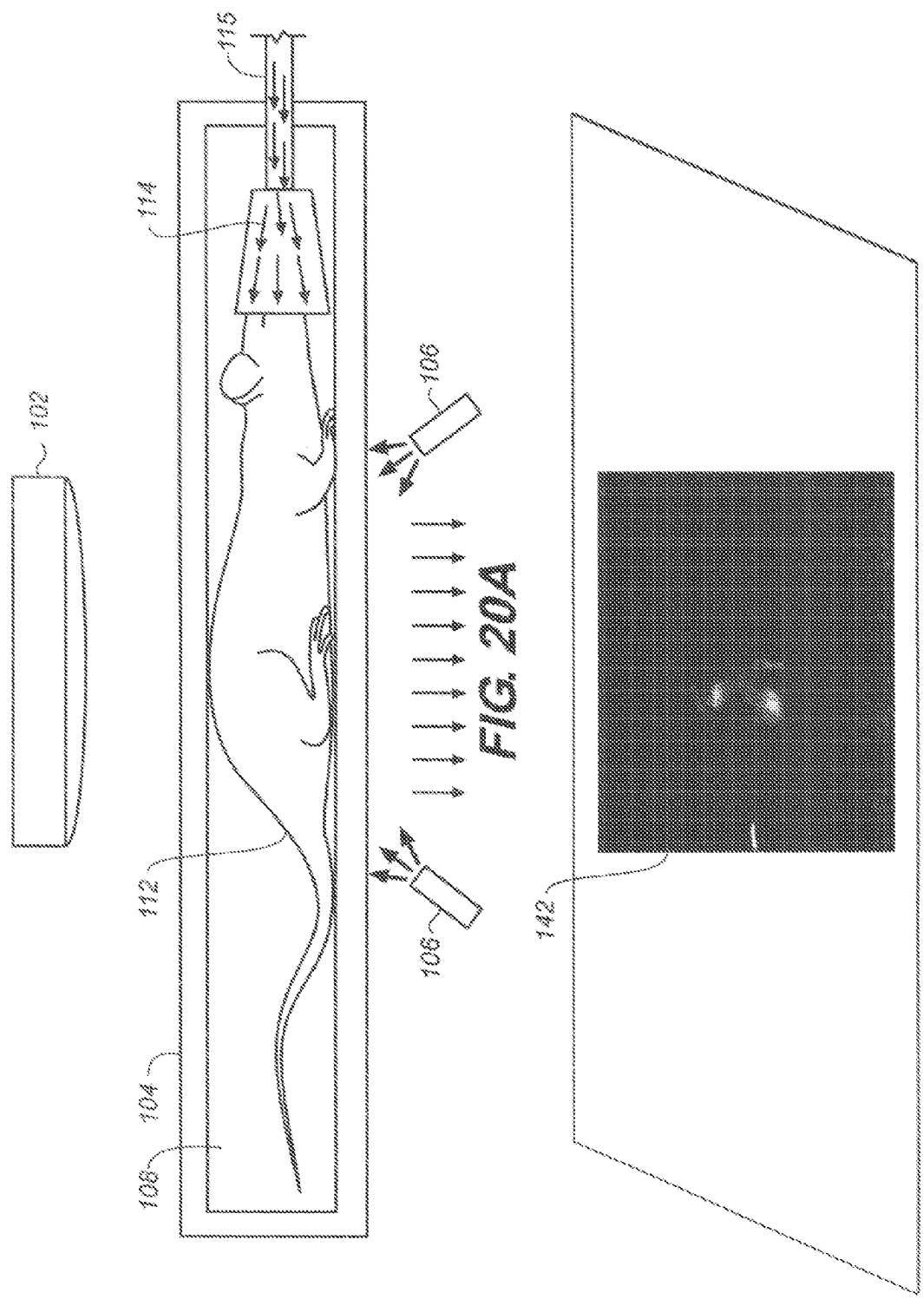
FIG. 20A shows a diagrammatic partial view of a mouse in a sample chamber on the sample object stage of the imaging system of FIGS. 3A and 1B when a near-infrared fluorescence image of the kidneys is acquired in accordance with the present invention.
FIG. 20B shows a near-infrared fluorescence image captured using the system of FIG. 20A.

An example of this strategy in practice is given in FIGS. 14A through 16B, previously discussed. In this case, the experimenter is attempting to localize a fluorescent signal with the gastrointestinal (GI) tract. Since this sizable organ yields poor contrast in an X-ray image, an x-ray contrast agent must be utilized. Agents such as barium sulfate have been used in the clinic for decades to resolve GI features. Since barium salts are generally insoluble and inert, they may be safely used in the human GI tract, either orally or rectally, to provide contrast during X-ray imaging. After imaging is complete, the barium is excreted from the subject without absorption into the body. However, the use of agents such as barium sulfate in small animal imaging has been minimal, and they have not been used in a multimodal approach to localize fluorescent or luminescent signals. The images shown in FIGS. 14B, 15B, 16A and 16B illustrate how contrast agents like barium sulfate may be utilized for the anatomical co-registration of fluorescent or luminescent signals during optical imaging. These figures show an example of a mouse after one hour of consumption of 40 mg of a 1:1 mixture of barium sulfate and creamy peanut butter combined with Kodak X-Sight 761 Nanospheres, which are near-infrared fluorescent nanoparticles (commercially available from Carestream Health, Inc.). In this case, the contrast agent and fluorescent nanoparticles were administered simultaneously. Subsequent experiments could possibly use the barium sulfate/peanut butter mix alone to determine the clearance of the original dose of fluorophore. FIGS. 14B and 16A show the X-ray image 140 with excellent barium sulfate contrast (Target/Non-Target=1.33) of the GI tract. The near-infrared fluorescence image 142 of FIGS. 15B and 16B show near-infrared fluorescence from the nanoparticles. In this case, the origin of the optical signal is coincident with barium sulfate contrast of the X-ray image 140.

In addition to barium sulfate, iodinated contrast agents as well as gold nanoparticles may be used as X-ray contrast agents for various tissues. Iodine is a synthetically accessible atom with sufficient electron density to yield X-ray contrast. Thus, it has been incorporated into several compounds that may be synthesized as water soluble through contrast agents. These reagents are generally used for the purposes of intravenous injection since they are not harmful, and will rinse out of the subject through the renal pathway. Several iodine based contrast agents are commercially available for use in humans for imaging of heart vasculature and other bulk tissues. FIGS. 17A to 17C, 19A and 19B, and 20A and 20B show the utilization one such agent, Visipaque™ (iodixanol) commercially available from GE Healthcare, to localize a fluorescent signal in the renal system of mice. The mouse was administered an intravenous injection of 200 μL of Visipaque (iodixanol) (320 mg/ml iodine) combined with Kodak X-Sight 670 Large Stokes Shift dye, which is a near-infrared fluorescent dye (commercially available from Carestream Health, Inc.). The contrast agent and dye concentrated in the kidneys thereby providing clear contrast in them.

Figure 22:
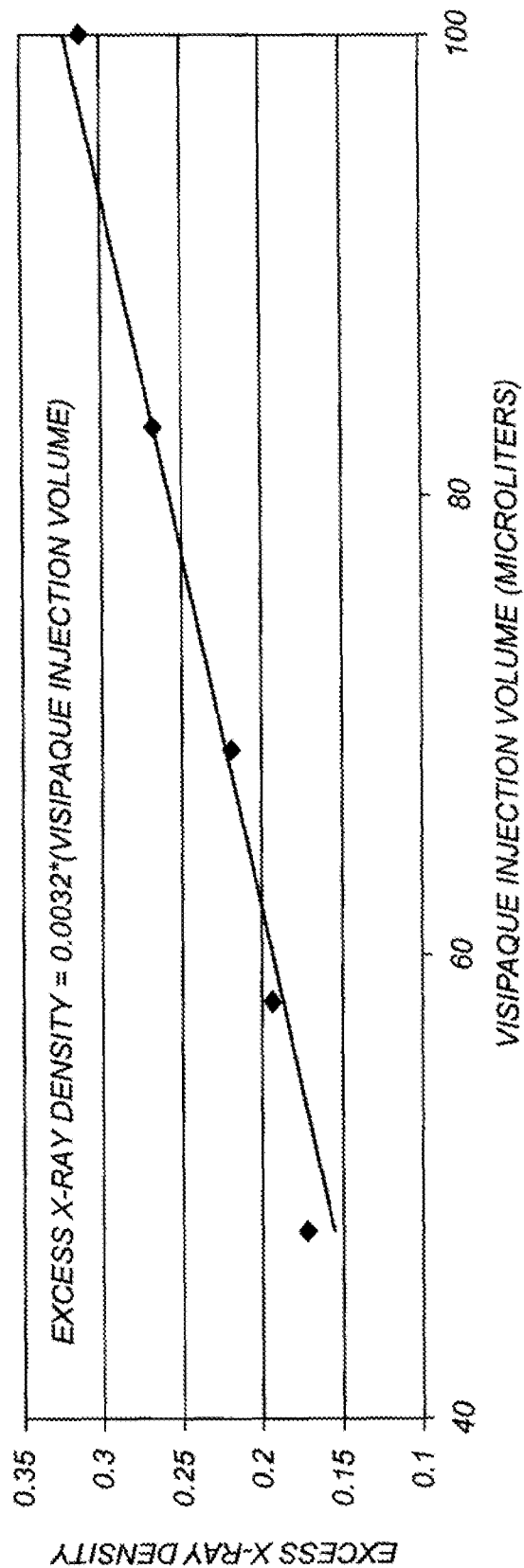
FIG. 22 shows a graph of the excess x-ray density in the medullary regions of the kidneys conferred by the X-ray contrast agent of FIG. 19 vs. the injected volume of the X-ray contrast agent.

FIG. 22 shows a graph of the excess x-ray density in the medullary regions of the kidneys conferred by the Visipaque vs. the injected volume of the Visipaque. Varying volumes of Visipaque were mixed with complementarily varying volumes of phosphate buffered saline to achieve a series of 200 μL total injection volumes. Mice were immobilized, and X-ray images were acquired both before and 10 minutes after injection of the different Visipaque injection volume for each mouse. The images before injection were subtracted from the images after injection corresponding to each mouse receiving a different Visipaque injection volume to create difference images, and a region-of-interest analysis was performed for the medullary regions of the kidneys in the difference images to measure the excess x-ray density conferred by the Visipaque in the medullary regions. The graph shows that the excess x-ray density in the medullary regions of the kidneys, wherein the excess x-ray density of both kidneys was averaged together for each mouse, is directly proportional to the injected volume of the Visipaque, with a constant of proportionality of 0.0032 as determined by a linear fit of the data.

As indicated earlier in this specification, the x-ray contrast agents and optical imaging agents may be targeted, non-targeted, or both. In accordance with the invention, the x-ray contrast agent may be targeted while the optical imaging agent is non-targeted; or the x-ray contrast agent may be non-targeted while the optical imaging agent is targeted; or both agents may be targeted; or both agents may be non-targeted. The following table lists the agents previously mentioned along with other known agents that the inventors consider appropriate for use in any convenient combination suited for an anatomical region of interest, without departing from the scope of the present invention.

| Agent | Modality | Targeted or Non-targeted | Anatomical Regions | Comments |
| --- | --- | --- | --- | --- |
| Barium sulfate | X-ray | Non-targeted | Gastrointestinal tract | Example in this spec |
| Barium sulfate in gelatin (Baritop) | X-ray | Non-targeted | Vasculature | |
| Iodinated contrast agents | X-ray | Non-targeted | Vasculature, renal | Example in this spec |
| Fenestra VC | X-ray | Non-targeted | Vasculature, renal | |
| Fenestra LC | X-ray | Non-targeted | Hepatobiliary | |
| eXIA 160 Radiocontrast | X-ray | Targeted | Vasculature | |
| eXIA 160 Radiocontrast | X-ray | Non-targeted | Hepatobiliary and Splenic | |
| Gold nanoparticles | X-ray | Non-targeted | Vasculature, renal, tumors | |
| Corrosion casting material Batson's 17 with added lead pigment | X-ray | Non-targeted | Vasculature | |
| Silicon rubber; Microfil MV122 | X-ray | Non-targeted | Vasculature | |
| Agents disclosed in U.S. Pat. No. 5,141,739 | X-ray | Targeted | Various | |
| Kodak X-Sight Nanospheres | Optical | Non-targeted | Gastrointestinal tract | Example in this spec |
| Kodak X-Sight Nanospheres | Optical | Non-targeted | Vasculature, hepatobiliary | Example in this spec |
| Kodak X-Sight large Stokes shift dyes | Optical | Non-targeted | Renal | Example in this spec |
| Kodak X-Sight Nanosphere Conjugates | Optical | Targeted | Various | |
| Kodak X-Sight large Stokes shift dye conjugates | Optical | Targeted | Various | |
| Qdots | Optical | Non-targeted | | |
| Qdot conjugates | Optical | Targeted | Vascular, hepatobiliary | |
| Various dyes | Optical | Non-targeted | Various | |
| Various dye conjugates | Optical | Targeted | Vascular | |
| Fluorescent silica | Optical | Non-targeted | Vasculature, renal, hepatobiliary | |
| Fluorescent silica conjugates | Optical | Targeted | Various | |
| Nanoparticles derived from self-assembly of amphiphilic copolymers | Optical | Non-targeted | Vascular, hepatobiliary | |
| Nanoparticles derived from self-assembly of amphiphilic copolymers | Optical | Targeted | Various | |
| Fluorescent proteins | Optical | Targeted | Various | |
| Luciferase | Optical | Targeted | Various | |

The X-ray contrast agents described herein, when used as disclosed, provide a facile methodology for the anatomical co-registration of both targeted and non-targeted fluorescent and luminescent signals during molecular imaging.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10 electronic imaging system
12 light source
14 optical compartment
16 mirror
18 lens and camera system
20 communication and computer control system
22 computer monitor
100 imaging system of the present invention
102 x-ray source
104 sample object stage or support member
106 epi-illumination; fiber optics
108 sample environment
110 access means/member
112 subject mouse
113 chamber for mouse 112
114 respiratory device
115 tube
116 rotational mechanism
117 translational mechanism
120 frame
122 support sheet
125, 125A phosphor plate
126 optical platen
128 protective layer
130 phosphor layer
132 optical layer
134 support plate; glass
136 air gap or void
138 air gap or void
140 X-ray image
142 near-infrared fluorescence image
144 X-ray image
146 near-infrared fluorescence image
148 co-registered image
150, 152, 156 potential secondary early detection sites
154 primary tumor injection site
200 to 208 method steps
210 transparent support
220 interference filter
240 thin phosphor layer
260 thick phosphor layer
280 opposite side
300 to 380 method steps
400 to 430 method steps

What is claimed is:

1. A method of imaging a subject animal, comprising:
treating the animal with an x-ray contrast agent and an optical imaging agent;
supporting the animal in an immobilized state on a support member;
providing a phosphor plate adapted to be disposed proximate the support member when capturing a first image;
with the phosphor plate disposed proximate the support member, imaging the immobilized animal in a first imaging mode to capture the first image, the first imaging mode being an x-ray mode;
removing the phosphor plate from proximate the support member, after capturing the first image and without moving the immobilized animal and the support member; and
with the phosphor plate removed from proximate the support member, imaging the immobilized animal in a second imaging mode to capture a second image, the second imaging mode being an optical dark-field mode.

2. The method of claim 1, further comprising the step of generating a third image by merging the first and second images, whereby features of the second image can be observed in relation to features of the first image.

3. The method of claim 1, wherein the x-ray contrast agent and the optical imaging agent are administered simultaneously to the animal.

4. The method of claim 1, wherein the x-ray contrast agent and the optical imaging agent are administered sequentially to the animal.

5. The method of claim 1, wherein the optical, dark-field image is a fluorescence image.

6. The method of claim 1, wherein the x-ray anatomical image and the optical, dark-field image are acquired using a common, shared focal plane.

7. The method of claim 1, wherein the x-ray contrast agent is targeted and the optical imaging agent is non-targeted.

8. The method of claim 1, wherein the x-ray contrast agent is non-targeted and the optical imaging agent is targeted.

9. The method of claim 1, wherein both the x-ray contrast agent and the optical imaging agent are targeted.

10. The method of claim 1, wherein both the x-ray contrast agent and the optical imaging agent are non-targeted.

11. A method of imaging a subject animal, comprising:
treating the animal with an x-ray contrast agent and an optical imaging agent;
supporting the animal in an immobilized state on a support member;
providing a phosphor plate movable relative to the support member, without disturbing the immobilized animal and the support member, between a first position wherein the phosphor plate is in optical registration with the support member and a second position wherein the phosphor plate is not in optical registration with the support member;
capturing an x-ray image of the immobilized animal when the phosphor plate in disposed in the first position; and
capturing an optical dark-field image of the immobilized animal when the phosphor plate in disposed in the second position.

12. The method of claim 11, further comprising:
generating a third image by merging the first and second images, whereby features of the second image can be observed in relation to features of the first image; and
displaying, transmitting, processing, or printing, the third image.

13. The method of claim 11, wherein the x-ray anatomical image and the optical, dark-field image are acquired using a common, shared focal plane.

14. An apparatus for imaging a subject animal, comprising:
first imaging means for imaging such an animal in a first imaging mode to capture a first image, the first imaging mode being selected from the group: x-ray mode and radio isotope mode;
second imaging means for imaging such an animal in a second imaging mode that uses light from the immobilized animal to capture a second image, the second imaging mode being selected from the group: bright-field imaging mode and dark-field imaging mode;

a support stage, fixedly mounted in the apparatus, for receiving such an animal in an immobilized state such that the animal is immobilized in the apparatus during imaging by the first and second imaging means without movement of the animal from the support stage or movement of the support stage between capture of the first and second images; and a movable phosphor plate to transduce ionizing radiation from the first imaging means to visible light, the phosphor plate being mounted to be moved, without moving the immobilized animal and support stage, between a first position proximate the support stage during capture of the first image and a second position not proximate the support stage during capture of the second image.

15. A method for imaging a subject animal, comprising:

providing a fixed support stage;

receiving the animal on the support stage in an immobilized state;

imaging the immobilized animal on the support stage in a first imaging mode to capture a first image, the first imaging mode being selected from the group: x-ray mode and radio isotope mode;

without moving the animal or the support stage, imaging the animal on the support stage in a second imaging mode that uses light from the immobilized animal to capture a second image, the second imaging mode being selected from the group: bright-field imaging mode and dark-field imaging mode;

providing a movable phosphor plate to transduce ionizing radiation from the first imaging means to visible light; and moving the phosphor plate, without moving the immobilized animal and support stage, between a first position proximate the support stage during capture of the first image and a second position not proximate the support stage during capture of the second image.

16. The method according to claim 15, further comprising:

treating the animal with an x-ray contrast agent and an optical imaging agent; and registering the first image with the second image, whereby features of the second image may be observed in relation to features of the first image.

* * * * *